(12) United States Patent
Tanaka et al.

(10) Patent No.: US 10,602,985 B2
(45) Date of Patent: Mar. 31, 2020

(54) CONTACT DETECTION INSTRUMENT

(71) Applicants: NAGOYA INSTITUTE OF TECHNOLOGY, Nagoya-shi, Aichi (JP); NATIONAL UNIVERSITY CORPORATION NAGOYA UNIVERSITY, Nagoya-shi, Aichi (JP)

(72) Inventors: Yoshihiro Tanaka, Nagoya (JP); Akihito Sano, Motosu-gun (JP); Michitaka Fujiwara, Nagoya (JP)

(73) Assignees: NAGOYA INSTITUTE OF TECHNOLOGY, Nagoya (JP); NATIONAL UNIVERSITY CORPORATION NAGOYA UNIVERSITY, Nagoya (JP)

( * ) Notice: Subject to any disclaimer, the term of this patent is extended or adjusted under 35 U.S.C. 154(b) by 448 days.

(21) Appl. No.: 15/505,997

(22) PCT Filed: Aug. 4, 2015

(86) PCT No.: PCT/JP2015/072097
§ 371 (c)(1),
(2) Date: Feb. 23, 2017

(87) PCT Pub. No.: WO2016/031503
PCT Pub. Date: Mar. 3, 2016

(65) Prior Publication Data
US 2017/0265814 A1 Sep. 21, 2017

(30) Foreign Application Priority Data
Aug. 26, 2014 (JP) .................... 2014-171878

(51) Int. Cl.
*A61B 5/00* (2006.01)
*A61B 8/12* (2006.01)
(Continued)

(52) U.S. Cl.
CPC ............ *A61B 5/6885* (2013.01); *A61B 5/042* (2013.01); *A61B 5/7415* (2013.01);
(Continued)

(58) Field of Classification Search
CPC ....... A61B 5/6885; A61B 8/445; A61B 90/06; A61B 34/76; A61B 17/00234;
(Continued)

(56) References Cited

U.S. PATENT DOCUMENTS 5,230,623 A * 7/1993 Guthrie ................ G06F 3/0346
33/513
6,083,163 A * 7/2000 Wegner ................ B25J 9/1679
600/429
(Continued)

FOREIGN PATENT DOCUMENTS

JP 2013-052046 A 3/2013

OTHER PUBLICATIONS

Oct. 27, 2015 Search Report issued in International Patent Application No. PCT/JP2015/072097.
(Continued)

*Primary Examiner* — Nimeshkumar D Patel
*Assistant Examiner* — Tania Courson
(74) *Attorney, Agent, or Firm* — Oliff PLC

(57) ABSTRACT

A contact detection instrument including a rod, a tip sensor portion that is attached to one end of the rod and is inserted into a living body through a hole, a speaker that, from outside the living body, inputs a sound into a hollow space that is formed in the interior of the rod and the tip sensor portion, and a microphone that, outside the living body, outputs an electrical signal that corresponds to the sound inside the hollow space, with the tip sensor portion including an elastic material that covers the hollow space.

14 Claims, 21 Drawing Sheets

(51) Int. Cl.
   *A61B 34/00* (2016.01)
   *A61B 90/00* (2016.01)
   *A61B 17/00* (2006.01)
   *A61B 8/00* (2006.01)
   *A61B 5/042* (2006.01)
   *A61M 25/00* (2006.01)
   *A61B 5/06* (2006.01)
   *A61B 5/107* (2006.01)
   *A61B 7/00* (2006.01)

(52) U.S. Cl.
   CPC .............. *A61B 5/7455* (2013.01); *A61B 8/12* (2013.01); *A61B 8/445* (2013.01); *A61B 17/00234* (2013.01); *A61B 34/76* (2016.02); *A61B 90/06* (2016.02); *A61M 25/0021* (2013.01); *A61B 5/065* (2013.01); *A61B 5/1076* (2013.01); *A61B 5/4238* (2013.01); *A61B 5/4887* (2013.01); *A61B 7/00* (2013.01); *A61B 2017/00022* (2013.01); *A61B 2017/00115* (2013.01); *A61B 2017/00973* (2013.01); *A61B 2090/065* (2016.02); *A61B 2505/05* (2013.01); *A61B 2562/0204* (2013.01); *A61M 2025/0002* (2013.01)

(58) Field of Classification Search
   CPC ..... A61B 5/7455; A61B 5/7415; A61B 5/042; A61B 8/12; A61B 2090/065; A61B 2562/0204; A61B 2505/05; A61B 2017/00973; A61B 2017/00115; A61B 2017/00022; A61B 5/4887; A61B 5/4238; A61B 5/1076; A61B 5/065; A61B 7/00; A61M 25/0021; A61M 2025/0002
   See application file for complete search history.

(56) References Cited

U.S. PATENT DOCUMENTS

| | | | | |
|---|---|---|---|---|
| 6,171,249 | B1* | 1/2001 | Chin | A61B 8/0833 600/143 |
| 6,447,447 | B1* | 9/2002 | Mitsumori | A61B 1/00188 600/129 |
| 6,733,464 | B2* | 5/2004 | Olbrich | A61B 5/0205 600/538 |
| 6,837,888 | B2* | 1/2005 | Ciarrocca | A61B 18/1402 606/32 |
| 7,857,811 | B2* | 12/2010 | Vaska | A61B 17/2202 33/512 |
| 8,070,681 | B2* | 12/2011 | Okumura | G10K 11/341 600/407 |
| 8,725,233 | B2* | 5/2014 | Nagano | A61B 5/6885 600/424 |
| 10,149,712 | B2* | 12/2018 | Manwaring | A61B 18/082 |
| 2003/0088186 | A1* | 5/2003 | Doody | A61B 5/053 600/547 |
| 2004/0077974 | A1* | 4/2004 | Moore | A61B 7/04 600/587 |
| 2004/0267121 | A1* | 12/2004 | Sarvazyan | A61B 5/4312 600/439 |
| 2010/0305664 | A1* | 12/2010 | Wingeier | A61N 1/36007 607/62 |
| 2014/0194923 | A1* | 7/2014 | Zemlok | A61B 17/07207 606/205 |
| 2015/0080764 | A1* | 3/2015 | Poe | A61B 1/00135 600/586 |
| 2018/0221610 | A1* | 8/2018 | Larson | A61B 1/00009 |
| 2018/0250086 | A1* | 9/2018 | Grubbs | A61B 34/37 |

OTHER PUBLICATIONS

Y. Tanaka et al., "Tactile Sensor Including Bidirectionality for Laparoscope-Assisted Surgery," Proceedings of the JSME Robotics and Mechatronics Conference 2013, 2A2-B02.

Tomohiro Fukuda et al., "A Study on Forceps-type Tactile Sensor Using Acoustic Reflection", Proceedings of the Annual Conference of the Robotics Society of Japan (DVD-ROM), vol. 31, The Robotics Society of Japan, Sep. 4, 2013 (Sep. 4, 2013), pp. ROMBUNN0. 3L1-05.

Jul. 11, 2016 International Preliminary Report on Patentability issued in International Patent Application No. PCT/JP2015/072097.

Oct. 27, 2015 Written Opinion issued in International Patent Application No. PCT/JP2015/072097.

* cited by examiner

CONTACT DETECTION INSTRUMENT

TECHNICAL FIELD

The present invention relates to a contact detection instrument and a sensing system. The contact detection instrument is inserted into a living body through a hole that has been opened in the surface of the living body, comes into contact with an internal organ inside the living body, and outputs a signal that corresponds to the state of the internal organ with which the instrument is in contact. The sensing system is provided with the contact detection instrument and with a tactile communication device that provides a tactile stimulus to a user. The contact detection instrument and the sensing system are suitable for use in laparoscopic surgery, for example.

BACKGROUND ART

A technology is known whereby, when a contact detection instrument is inserted into a living body through a hole that has been opened in the surface of the living body and the contact detection instrument comes into contact with an internal organ inside the living body, a signal is output from the contact detection instrument that corresponds to the state of the internal organ with which the instrument is in contact.

For example, in NPL 1, a contact detection instrument is disclosed in which a PVDF film, which is a type of macromolecular piezoelectric material, is attached to a tip of a pair of forceps. A sensor signal that corresponds to the pressure on the PVDF film when it comes into contact with an internal organ is output from the contact detection instrument.

CITATION LIST

Non-Patent Literature

[NPL 1]
Y. Tanaka, T. Nagai, M. Fujiwara, A. Sano, Tactile Sensor Including Bidirectionality for Laparoscope-Assisted Surgery, Proceedings of the JSME Robotics and Mechatronics Conference 2013, 2A2-B02.

SUMMARY OF INVENTION

Technical Problem

However, with a contact detection instrument like that described above, an electrical signal is generated inside a living body, which presents a problem from the standpoint of the safety of the living body. In light of this problem, it is an object of the present invention to provide more safety for the living body with a contact detection instrument that is inserted into the living body through a hole that has been opened in the surface of the living body, comes into contact with an internal organ inside the living body, and outputs a signal that corresponds to the state of the internal organ with which the instrument is in contact.

Solution to Problem

In order to achieve the object stated above, the contact detection instrument of the present invention is a contact detection instrument that is to be inserted into an interior of a living body (91) through a hole (91c) that has been opened in the living body (91), and it is provided with a rod (12), a tip sensor portion (20, 20', 20'', 20''') that is attached to one end of the rod (12) and is to be inserted into the interior of the living body (91) through the hole (91c), a speaker (14) that, from outside the living body (91), inputs a sound into a hollow space (11b to 11g, 12a) that is formed in interiors of the rod (12) and the tip sensor portion (20, 20', 20'', 20'''), and a microphone (15) that, outside the living body (91), outputs an electrical signal that corresponds to the sound inside the hollow space (11b to 11g, 12a). The tip sensor portion (20, 20', 20'', 20''') includes an elastic material (10, 10', 10'', 10''') that covers the hollow space (11b to 11g, 12a).

When this sort of contact detection instrument is used, the tip sensor portion is inserted into the living body through the hole that has been opened in the living body, and as the speaker is used to input the sound into the hollow space, the elastic material is brought into contact with an internal organ of the living body. The elastic material is thus deformed in accordance with the state (the shape, the hardness, and the like) of the internal organ that is being touched, and the reflection rate of the sound inside the hollow space changes as a result. For example, if the internal organ with which the elastic material is in contact is a comparatively hard internal organ like a lump, the internal organ that is being touched presses the elastic material inward into the hollow space, with the result that the path for the sound within the hollow space is narrowed and the reflection rate of the sound within the hollow space changes. Therefore, the signal that the microphone outputs changes in accordance with the state of the internal organ that is being touched. Moreover, because the sound is input into the hollow space from outside the living body, and the signal is output outside of the living body in accordance with the sound in the hollow space, no electrical signal is generated inside the living body. Therefore, the safety of the living body is better than with the known technology.

Note that the reference signs in parentheses above and in the claims indicate correspondence relationships between the terms that are used in the claims and concrete objects and the like that exemplify the terms that are used hereinafter in the description of the embodiments.

DESCRIPTION OF EMBODIMENTS (First Embodiment)

Figure 1:
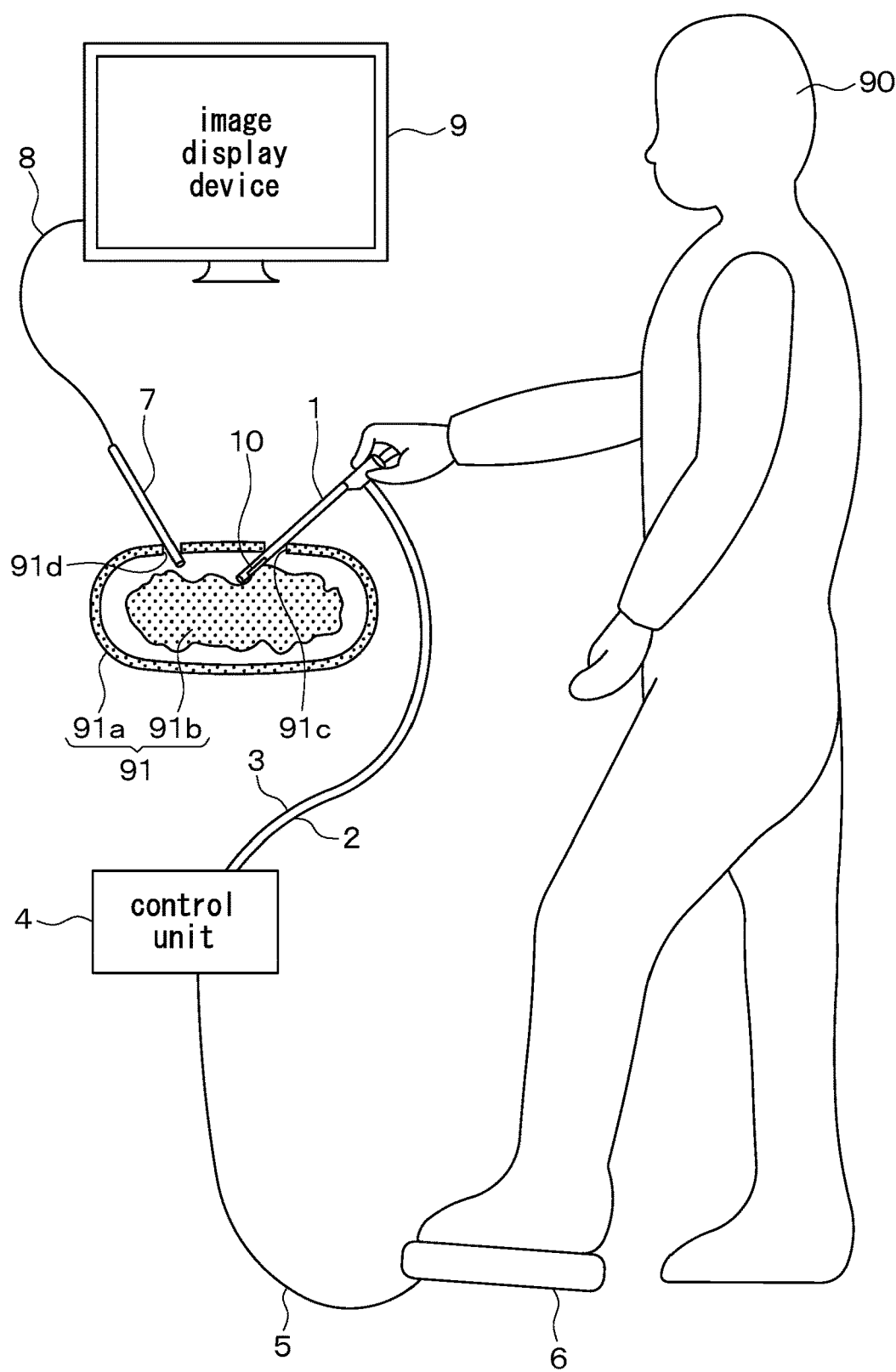
FIG. 1 is a figure that shows the entire configuration of a sensing system according to a first embodiment of the present invention.

Hereinafter, a first embodiment of the present invention will be described. A sensing system of the present embodiment is used in laparoscopic surgery, and as shown in FIG. 1, it includes a contact detection instrument 1, a cable 2, a cable 3, a control unit 4, a cable 5, a haptic presentation device 6, an endoscope 7, a cable 8, and an image display device 9.

In laparoscopic surgery, a plurality of holes (for example, holes 91c, 91d) having diameters of about five to twelve millimeters are opened in a skin 91a on the surface of a living body 91 of a person or the like. Of plurality of holes, the hole 91d is the one through which the endoscope 7 is inserted into the interior of the living body 91. An electric scalpel, forceps, and the like (not shown in the drawings) are inserted into the interior of the living body 91 through other holes (not shown in the drawings) among the plurality of the holes.

During the surgery, the endoscope 7 captures an image an internal organ 91b on which the surgical procedure is being performed inside the living body 91. Through the cable 8, the image display device 9 acquires the image of the internal organ 91b (for example, the stomach) that the endoscope 7 has captured and displays the image to an operator 90. While looking at the image, the operator 90 performs the surgical procedure on the internal organ 91b by operating the electric scalpel and the forceps from outside the living body 91.

Although this sort of laparoscopic surgery is a minimally invasive therapy, it is largely limited by the tactile sensing of the operator 90. If the tactile sensing could be complemented, it would become possible to identify the site of a tumor by palpation, as is done in conventional open abdominal surgery. This would make it possible to prevent problems such as leaving a portion of a tumor unremoved or excising more tissue than is necessary, so improvements in minimally invasive therapy could be anticipated.

The inclusion of the contact detection instrument 1, the cable 2, the cable 3, the control unit 4, the cable 5, and the haptic presentation device 6 makes it possible for the sensing system of the present embodiment to complement the tactile sensing of the operator 90 by combining the receiving of tactile information by the human sense of touch with bidirectionality of operation.

To achieve this, the operator 90 inserts a portion of the contact detection instrument 1 into the interior of the living body 91 through a trocar (not shown in the drawings) that has been inserted into the hole 91c, which is one of the plurality of the holes described above. The operator 90 then manipulates the contact detection instrument 1 from outside the living body 91, such that an elastic film 10 (which is equivalent to an example of an elastic material) that is attached to the contact detection instrument 1 traces the contour of the internal organ 91b. A tactile sensation that corresponds to the contour of the internal organ 91b that is traced by the elastic film 10 is thus provided to the operator 90 by the haptic presentation device 6.

Figure 2:
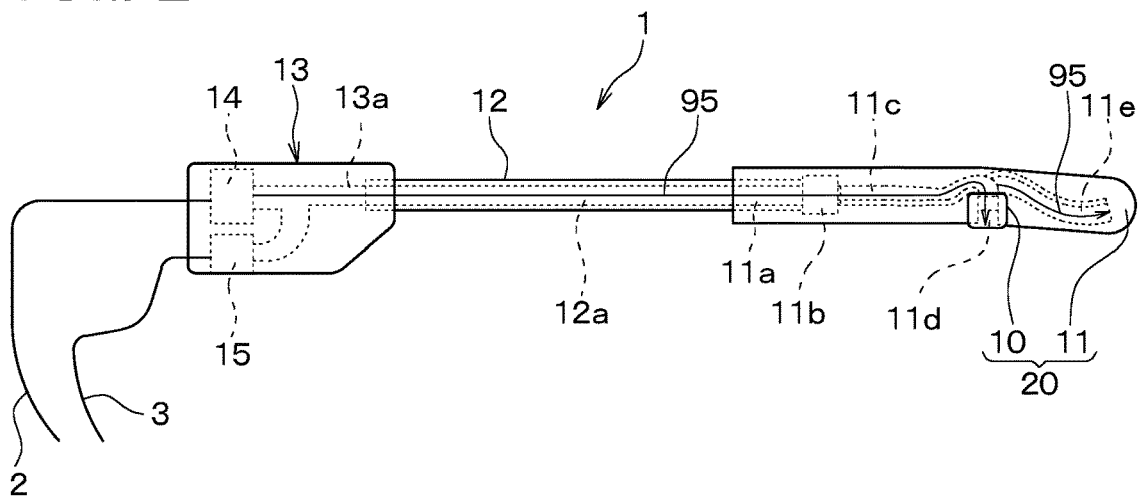
FIG. 2 is a figure that shows the configuration of a contact detection instrument 1.

First, the configuration of the contact detection instrument 1 will be explained with reference to FIG. 2. As shown in FIG. 2, the contact detection instrument 1 is a forceps-shaped instrument that includes a tip sensor portion 20, a rigid tube 12, a grip portion 13, a speaker 14, and a microphone 15. The tip sensor portion 20 is configured from the elastic film 10 and a tip base portion 11. The tip sensor portion 20 extends nearly straight along the axis along which the rigid tube 12 extends, but it is slightly curved, in the same manner as forceps.

The grip portion 13 is an ABS resin member, for example, that the operator 90 holds directly with his fingers during the surgical procedure, and the speaker 14 and the microphone 15 are embedded in the interior of the grip portion 13. The grip portion 13 is the portion of the contact detection instrument 1 that is not inserted into the living body 91 through the hole 91c.

The rigid tube 12 is a hollow cylindrical rod with no bottom, open at both ends, that extends straight from the grip portion 13, with one end inserted into the grip portion 13 and secured. The material for the rigid tube 12 may be aluminum, for example. The width of the rigid tube 12 is such that it can be passed through the trocar that has been inserted into the hole 91c, with an outside diameter of 5 millimeters, for example, and an inside diameter of 3 millimeters. The other end of the rigid tube 12 is inserted into the tip base portion 11 and secured. The portion of the rigid tube 12 that is toward the grip portion 13 is the portion that is not inserted into the living body 91 through the hole 91c, and the portion of the rigid tube 12 that is toward the tip base portion 11 is the portion that is inserted into the living body 91 through the hole 91c.

The tip base portion 11 is an ABS resin member, for example, that extends either straight or with a slightly curvature along the same axis as the rigid tube 12. The width of the tip base portion 11 is such that it can be passed through the hole 91c, with an outside diameter of 7 millimeters, for example. The length of the tip base portion 11 may be 70 millimeters, for example.

The elastic film 10 is attached to the tip base portion 11. The elastic film 10 is also a portion that is inserted into the living body 91 through the hole 91c. The elastic film 10 is a thin film member that is made from an elastic material such as silicone rubber or the like, and it is a portion that is inserted into the living body 91 through the hole 91c. The thickness of the elastic film 10 may be 0.5 millimeters, for example, and its Young's modulus may be 0.2 MPa, for example.

The method by which the operator 90 manipulates the contact detection instrument 1 will now be explained. The operator 90 holds the grip portion 13 with his fingers and, starting from the tip base portion 11, inserts the contact detection instrument 1 into the trocar (not shown in the drawings) inside the hole 91c. The entire tip sensor portion 20 and a portion of the rigid tube 12 are thus inserted into the living body 91 through the hole 91c.

Figure 3:
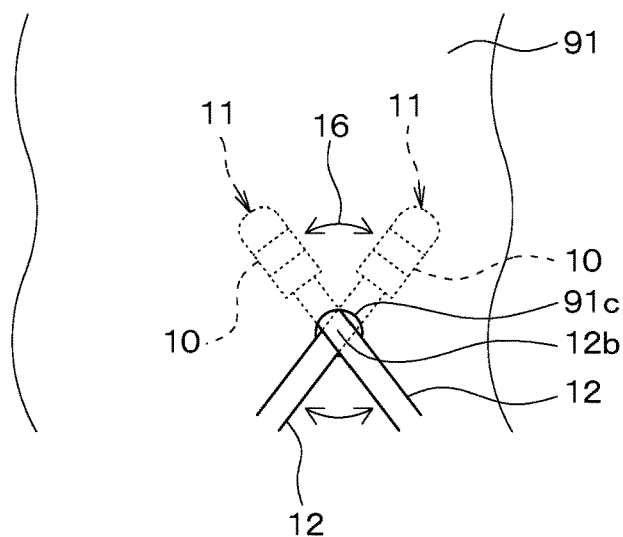
FIG. 3 is a figure that shows a movement path 16 of the contact detection instrument 1 during a surgical procedure.

Then, during the surgical procedure, the operator, in order to search for a lump within the internal organ 91b, moves the contact detection instrument 1 to the left and the right, with the hole 91c as the pivot point, as shown in FIG. 3, while keeping the elastic film 10b in contact with the internal organ 91b. During this process, the length of the portion of the contact detection instrument 1 that is inserted into the living body 91 through the hole 91c varies only slightly or not at all.

Moving the contact detection instrument 1 in a fan-shaped pattern like this causes the elastic film 10 to travel along an arc-shaped movement path 16 as it follows the contour of the internal organ 91b. Note that, in laparoscopic surgery, in the search for a lump within the internal organ 91b, the contact detection instrument 1 is moved only slightly in the direction of insertion into the hole 91c (that is, the longitudinal direction of the rigid tube 12 and the longitudinal direction of the trocar).

Returning to the explanation of the configuration of the contact detection instrument 1, hollow spaces are formed in the interiors of the grip portion 13, the rigid tube 12, and the tip sensor portion 20. Specifically, a hollow space 13a is formed in the interior of the grip portion 13, a hollow space 12a is formed in the interior of the rigid tube 12, and hollow spaces 11b, 11c, 11d, 11e are formed in the interior of the tip base portion 11. Furthermore, the hollow spaces 11b to 11e, 12a, 13a form a single continuous hollow space with a total length of 360 millimeters.

The hollow space 13a in the interior of the grip portion 13 has openings in only three locations, one where the rigid tube 12 is connected to the grip portion 13, one where the speaker 14 is attached, and one where the microphone 15 is attached.

The hollow space 12a in the interior of the rigid tube 12 is a cylindrical open space that extends straight and has a diameter of 3 millimeters. The rigid tube 12 has openings in only two locations, one where the grip portion 13 is connected to the rigid tube 12 and one where the tip base portion 11 is connected to the rigid tube 12, and it has a cylindrical shape that extends straight in the longitudinal direction of the rigid tube 12. The opening in the hollow space 12a where the grip portion 13 is connected to the rigid tube 12 is connected to the corresponding opening in the hollow space 13a, such that the hollow space 12a and the hollow space 13a are continuous with one another.

A side view, an oblique view, and section views of the tip base portion 11 are shown in FIGS. 4 to 9. Note that in FIGS. 5 to 9, the rigid tube 12 and the elastic film 10 have been omitted. A connecting hole 11a and the hollow spaces 11b, 11c, 11d, 11e are formed in the interior of the tip base portion 11, with the hollow spaces 11b, 11c, 11d, 11e being continuous with one another, such that they form a single hollow space.

The connecting hole 11a is a cylindrical hole that has openings in only two locations in the portion where the rigid tube 12 and the tip base portion 11 are connected. Specifically, the connecting hole 11a has a circular opening 11a-1 in the end of the tip base portion 11 that is closest to the grip portion 13. The connecting hole 11a also has a circular opening 11a-2 in the opposite end of the rigid tube 12 from the grip portion 13.

The connecting hole 11a extends straight along the longitudinal direction of the tip base portion 11 (the left-right direction in FIG. 4), coaxially with the outer form of the tip base portion 11, and connects with the opening in the hollow space 11b at the circular opening 11a-2 to become continuous with the hollow space 11b. Note that in a state in which the rigid tube 12 is completely inserted into the connecting hole 11a (refer to FIGS. 3, 4), the rigid tube 12 occupies a portion of the connecting hole 11a, and the remaining portion of the connecting hole 11a overlaps with the hollow space 12a.

The hollow space 11b is a cylindrical open space that extends from an opening at the connecting hole 11a end straight toward the tip of the contact detection instrument 1 (toward the right in FIG. 4), extending coaxially with the connecting hole 11a and having a larger diameter than the connecting hole 11a. The hollow space 11b also has an opening in the end toward the tip of the contact detection instrument 1, and it is connected to the hollow space 11c. The hollow space 11b and the hollow space 11c are thus continuous with one another.

Figure 4:
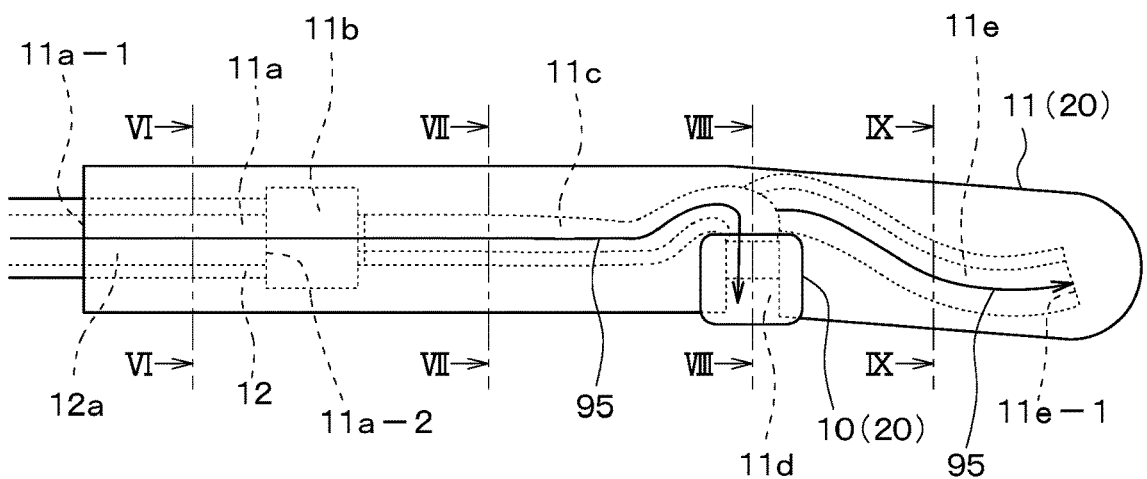
FIG. 4 is a side view of a tip base portion 11.
Figure 5:
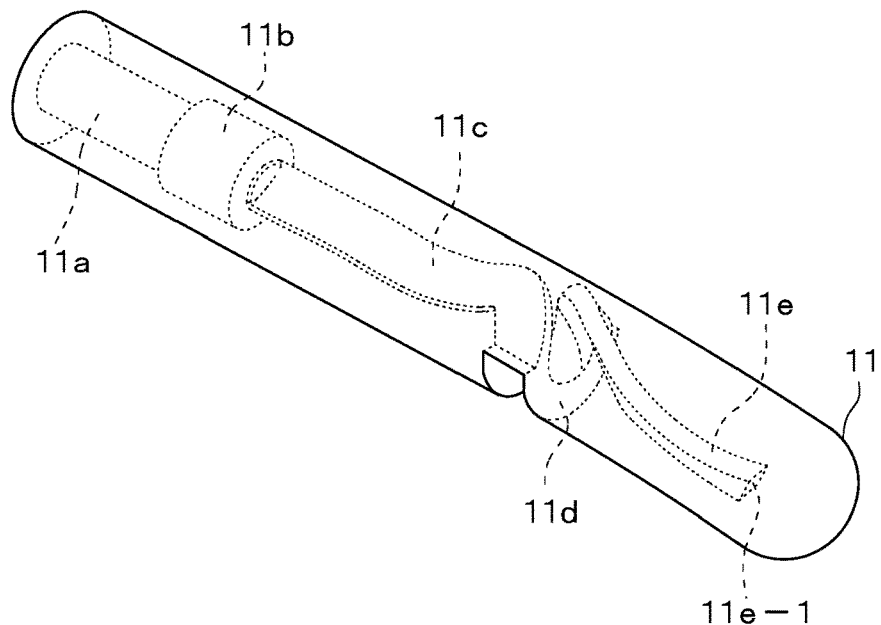
FIG. 5 is an oblique view of the tip base portion 11.
Figure 6:
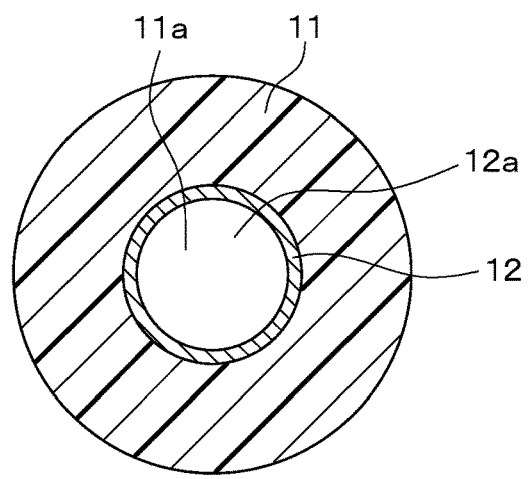
FIG. 6 is a section view at the line VI-VI in FIG. 4.
Figure 7:
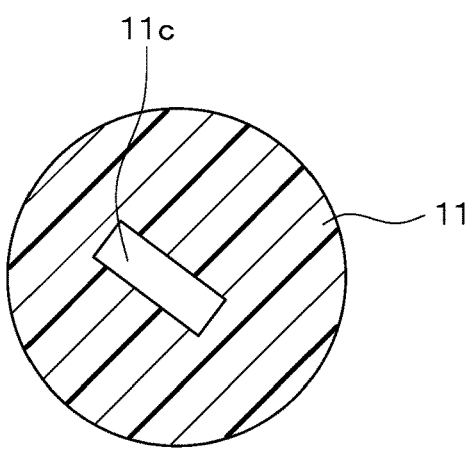
FIG. 7 is a section view at the line VII-VIII in FIG. 4.

The hollow space 11c extends from an opening at the hollow space 11b end, extending in a smoothly curving shape toward the tip end of the contact detection instrument 1 (the right end in FIG. 4). The hollow space 11c also has an opening in the end toward the tip of the contact detection instrument 1, and it is connected to the hollow space 11d. The hollow space 11c and the hollow space 11d are thus continuous with one another. Note that a vertical cross section of the hollow space 11c in the longitudinal direction of the hollow spaces is rectangular.

In an area that is close to the tip of the contact detection instrument 1 and is set apart from the central axis of the tip base portion 11, the hollow space 11d extends in an arc shape along a circumferential direction 96 of the tip sensor portion 20 for one-half of the circumference of the tip base portion 11. At one end of the circumferential direction 96, the hollow space 11d has an opening that connects to the opening in the hollow space 11c, and at the other end of the circumferential direction 96, the hollow space 11d has an opening that connects to an opening in the hollow space 11e. The elastic film 10 is attached to the tip base portion 11 such that it covers and seals off the hollow space 11d. Accordingly, when the elastic film 10 is pressed from outside the contact detection instrument 1, the elastic film 10 is deformed such that it is pressed inward toward the hollow space 11*d*.

The hollow space 11*e* has only one opening, which connects to the corresponding opening in the hollow space 11*d*, and the hollow space 11*e* extends from that opening in a smoothly curving shape toward the tip end of the contact detection instrument 1. The opposite end of the hollow space 11*e* from the opening is a fixed end 11*e*-1.

In order for the contact detection instrument 1 to achieve high sensitivity as a sensor, it is desirable for the distance to the sensing position (the position of the elastic film 10) from the position of the end (the fixed end 11*e*-1) of the hollow spaces (the position where sound is reflected) to be adjustable. In the present embodiment, the hollow space 11*e* at the tip end of the contact detection instrument 1 extends from the hollow space 11*d*, which is covered by the elastic film 10, so the distance can be adjusted easily. In the present embodiment, the position that is 25 millimeters from the fixed end 11*e*-1 in the longitudinal direction of the hollow spaces is actually located within the hollow space 11*d*, which is covered by the elastic film 10. A vertical cross section of the hollow space 11*e* in the longitudinal direction of the hollow spaces is rectangular.

Figure 8:
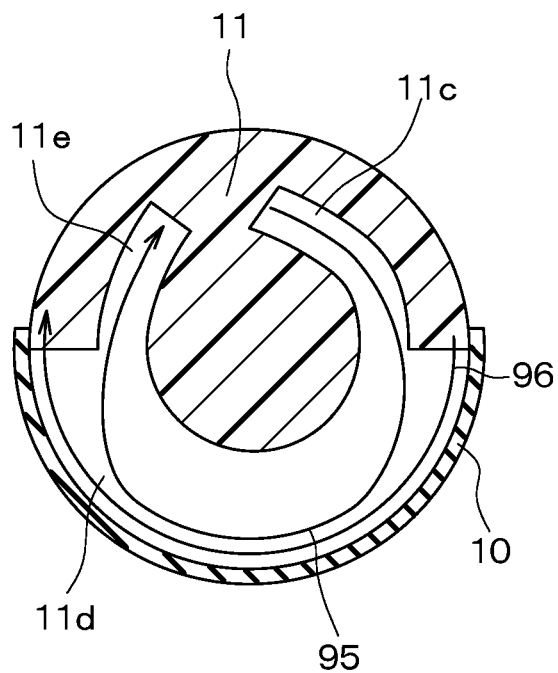
FIG. 8 is a section view at the line VIII-VIII in FIG. 4.
Figure 9:
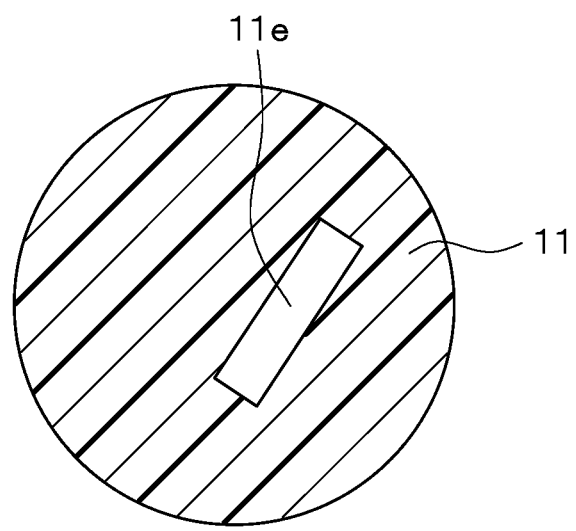
FIG. 9 is a section view at the line IX-IX in FIG. 4.

As explained previously, the hollow spaces 11*b* to 11*e*, 12*a*, 13*a* that are formed as described above form a single hollow space, and the longitudinal direction of the hollow spaces 11*b* to 11*e*, 12*a*, 13*a* is the direction that is indicated by arrows 95 in FIGS. 2, 4, and 8. Further, sound that is input into the hollow spaces from the speaker 14 is transmitted along the longitudinal direction 95.

The application of voltage from the control unit 4 to the speaker 14 through the cable 2 causes the speaker 14 to input sound into the hollow spaces 11*b* to 11*e*, 12*a*, 13*a*. A Kingstate KDMG10008C-03, for example, may be used as the speaker 14.

Through the cable 3, the microphone 15 outputs to the control unit 4 an electrical signal that corresponds to sound that is generated inside the hollow spaces 11*b* to 11*e*, 12*a*, 13*a*. An ICC/Intervox MEU-65PD-02-794, for example, may be used as the microphone 15.

The control unit 4 applies the voltage to the speaker 14 through the cable 2, acquires the electrical signal that the microphone 15 has output through the cable 3, and based on the acquired electrical signal, inputs control commands to the haptic presentation device 6, thereby controlling the haptic presentation device 6. This sort of control unit 4 can be implemented using a known microcomputer, personal computer, or workstation, for example.

Next, the configuration of the haptic presentation device 6 will be explained with reference to FIGS. 10 to 12. The haptic presentation device 6 of the present embodiment is a haptic display that transmits tactile information to the lower body of the operator 90, or more specifically, to the sole of the foot.

Figure 10:
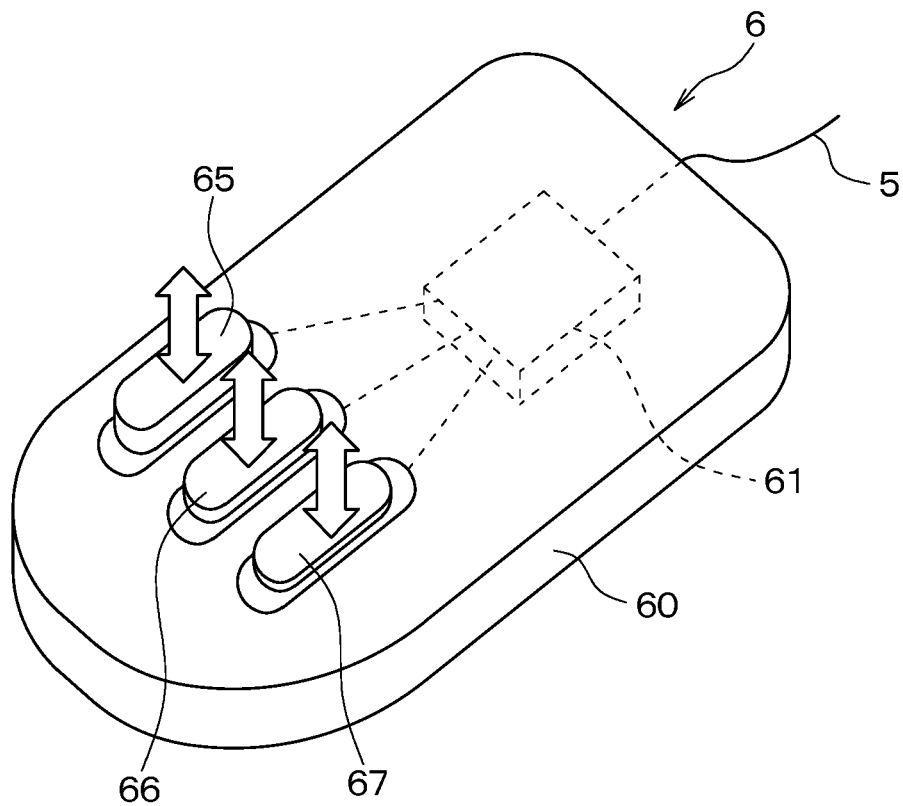
FIG. 10 is an oblique view of a haptic presentation device 6.
Figure 11:
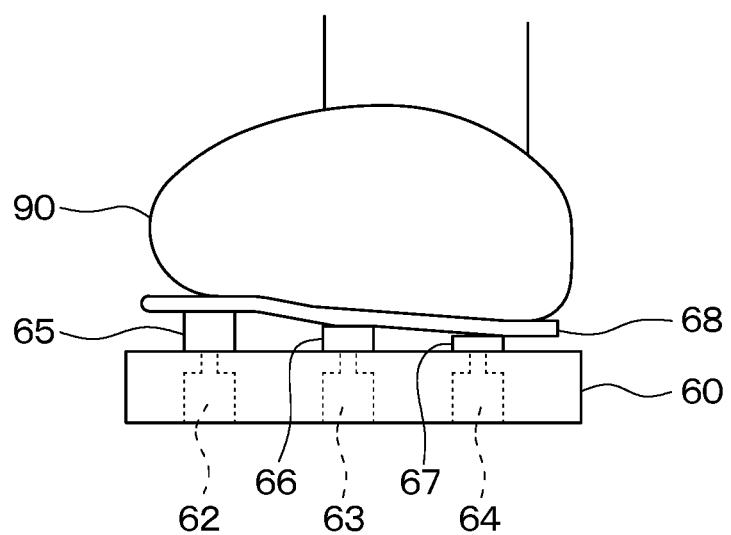
FIG. 11 is a front view of the haptic presentation device 6.
Figure 12:
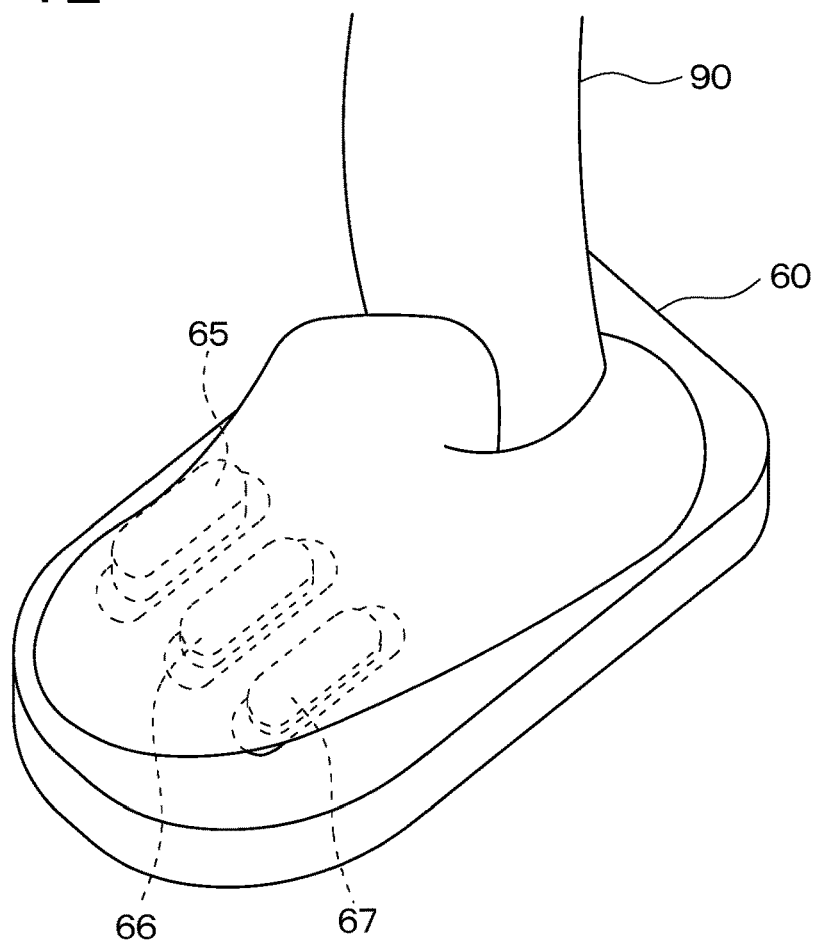
FIG. 12 is an oblique view of a state in which a foot of an operator 90 is placed on the haptic presentation device 6.

As shown in FIGS. 10 to 12, the haptic presentation device 6 includes a body portion 60, which is placed on the floor and on which the entire foot of the operator 90 rests, a drive circuit 61, which is disposed in the interior of the body portion 60, and three actuators 62, 63, 64, which are connected to the drive circuit 61. The haptic presentation device 6 also includes three stimulators 65, 66, 67, which are displaced by being driven by the actuators 62, 63, 64, respectively, the displacing of the stimulators 65, 66, 67 serving to provide tactile stimuli to the sole of the foot of the operator 90. The foot is placed on the body portion 60 in the manner shown in FIG. 12.

The drive circuit 61 drives the actuators 62 to 64 in accordance with the control commands that are output from the control unit 4 through the cable 5. The actuators 62 to 64 are devices that operate in accordance with the driving by the drive circuit 61 to displace the stimulators 65, 66, 67, respectively, in the up-down direction (the up-down direction in FIG. 11; refer to the arrows in FIG. 10).

The stimulators 65, 66, 67 are disposed in the left-right direction in the portion of the body portion 60 where the front end portion of the sole of the foot rests. When the positions of the stimulators 65, 66, 67 change in the up-down direction, the operator 90 recognizes the changes in the tactile stimuli to the front end portion of the sole of the foot.

Note that a flexible cover 68 that covers all of the stimulators 65, 66, 67 may be interposed between the stimulators 65, 66, 67 and the sole of the foot, as shown in FIG. 11. A flexible cover that is used in a haptic presentation device has been disclosed in H. Iwata, H. Yano, F. Nakaizumi, and R. Kawamura, "Project FEELEX: Adding Haptic Surface to Graphics," Proceedings of the 28th Annual Conference on Computer Graphics and Interactive Techniques, 469-476, 2001, for example. The interposing of the flexible cover 68 enables haptic presentation in which the positions and sizes of protrusions and depressions change smoothly.

The configuration of the sensing system in the present embodiment is as described above. Next, the detection principle in the sensing system of the present embodiment will be explained with reference to FIG. 13.

Figure 13:
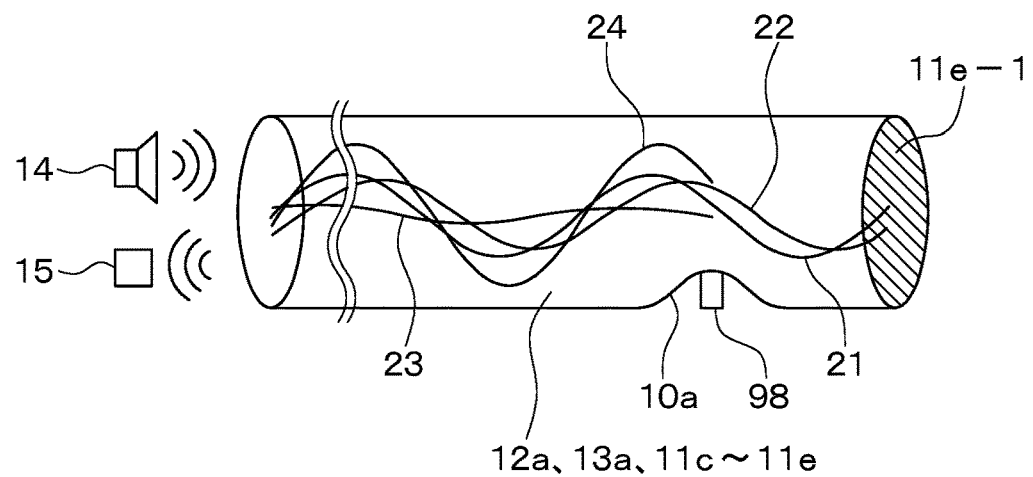
FIG. 13 is a schematic view that shows a principle of detection in the sensing system.

In FIG. 13, the hollow spaces 11*b* to 11*e*, 12*a*, 13*a* of the present embodiment are expressed schematically as a cylindrical pipe. When sound is input into the pipe from the speaker 14, the sound is reflected by the fixed end 11*e*-1 (the same as the fixed end 11*e*-1 in FIG. 4). At this time, if the side face of the pipe (which is equivalent to the elastic film 10) is deformed by a hard lump 98 and pressed inward into the hollow space, a protrusion 10*a* is formed inside the pipe, narrowing the path for the sound, and a portion of the sound is reflected by the protrusion 10*a*. Accordingly, if the sound in the pipe is measured by the microphone 15, information pertaining to the deformation of the pipe (the deformation amount and the deformation position) can be acquired.

Specifically, if an input sound 21 that is input to the pipe is defined as a sine wave with an amplitude $A_{in}$ and a frequency $f_{in}$, the sound inside the pipe becomes a composite sound 24 that is a composite of the input sound 21, a reflected sound 22 that is created by the reflecting of the input sound 21 by the fixed end 11*e*-1, and a reflected sound 23 that is created by the reflecting of the input sound 21 by the protrusion 10*a*.

Accordingly, an intensity $y_{out}$ of the composite sound 24 is expressed as follows:

$$y_{out} = A_{out} \sin(2\pi f_{in} t + \phi) \quad (1)$$

Here, $A_{out}$ is expressed by Equation (2) below, and the quantity $\phi$, which expresses the phase difference of the composite sound 24 in relation to the input sound 21, is expressed by Equation (3) below.

[Formula 1]

$$A_{out}^2 = 2A_{in}^2 \left\{ r^2 - r + 1 - (1-r)\cos\frac{4\pi f_{in} L}{v} - r\cos\frac{4\pi f_{in}(L-x_p)}{v} + r(1-r)\cos\frac{4\pi f_{in} x_p}{v} \right\} \quad (2)$$

-continued

[Formula 2]

$$\tan\phi = \frac{-(1-r)\sin\frac{4\pi f_{in}L}{v} - r\sin\frac{4\pi f_{in}(L-x_p)}{v}}{1-(1-r)\cos\frac{4\pi f_{in}L}{v} - r\cos\frac{4\pi f_{in}(L-x_p)}{v}} \quad (3)$$

Note that r is the reflection rate (0≤r≤1), which is determined according to the deformation amount, L is the total length of the pipe, xp is the distance to the deformation position from the tip of the pipe (that is, from the fixed end 11e-1), and v is velocity of sound inside the pipe. Based on Equations (1) to (3), a clear correlation can be seen between the amplitude $A_{out}$ and the phase difference φ of the composite sound 24 and the reflection rate r and the deformation position xp.

Figure 14:
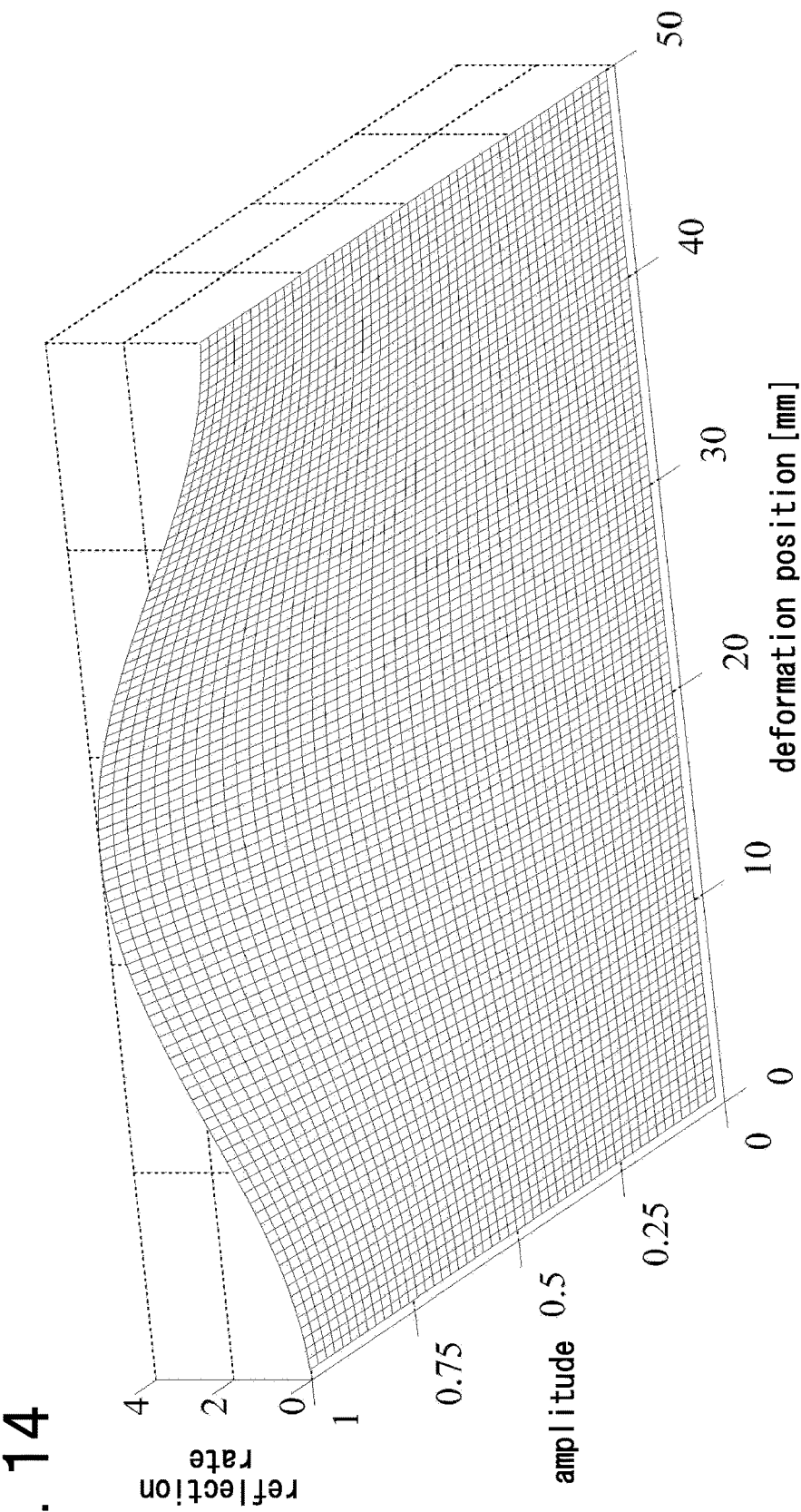
FIG. 14 is a figure that shows the behavior of an amplitude $A_{out}$ in relation to a reflection rate r and a deformation position xp.
Figure 15:
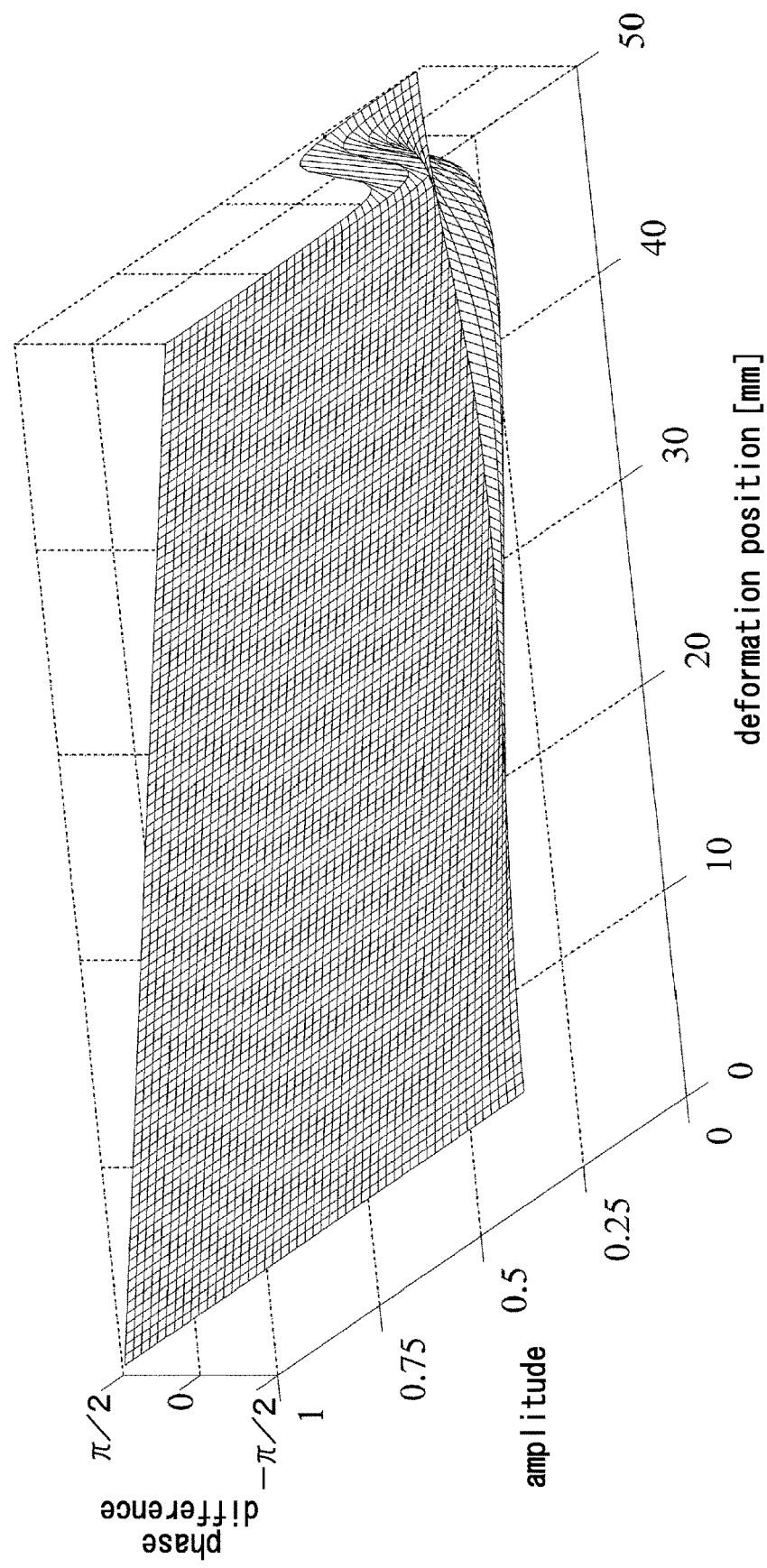
FIG. 15 is a figure that shows the behavior of a phase difference φ in relation to the reflection rate r and the deformation position xp.

Actually, in Equations (1) to (3), if L is defined as 360 millimeters, v is defined as 340 meters/second, and $f_{in}$ is defined as 3300 Hz, the behavior of the amplitude $A_{out}$ in relation to the reflection rate r and the deformation position xp is as shown in FIG. 14, and the behavior of the phase difference φ in relation to the reflection rate r and the deformation position xp is as shown in FIG. 15.

According to FIG. 14, in a case where the deformation position xp is not less than 20 millimeters and not greater than 30 millimeters, it can be seen that the deformation position xp has an almost independent correlation with the amplitude $A_{out}$ and the reflection rate r. Further, according to FIG. 15, it can be seen that the amplitude $A_{out}$ has an almost independent correlation with the phase difference φ and the deformation position xp. In other words, the phase difference φ can be treated as a quantity that expresses the deformation position xp, and the amplitude $A_{out}$ can be treated as a quantity that expresses that deformation amount (or the reflection rate r). Accordingly, the deformation amount (which correlates to the reflection rate r) and the deformation position xp can be measured almost independently.

Based on these facts, in the present embodiment, assume, for example, that the total length L of the hollow spaces 11b to 11e, 12a, 13a is 360 millimeters, and that the frequency $f_{in}$ of the input sound (the sine wave) from the speaker 14 to the hollow spaces 11b to 11e, 12a, 13a is 3300 Hz. Furthermore, assume that the elastic film 10 is attached to the tip base portion 11 such that it covers and seals off a range along the longitudinal direction of the hollow spaces 11b to 11e, 12a, 13a that is not less than 20 millimeters and not more than 30 millimeters from the fixed end 11e-1, or that the elastic film 10 covers and seals off only the hollow space 11d. However, it is clear that the applicable scope of the present invention is not limited to this example.

Note that while the case of a single tone ($f_{in}$=3300 Hz) was described above, it is also possible to input a plurality of sounds at a plurality of different frequencies, detecting the amplitude and the phase difference for each of the different input sounds and the composite sound, such that the deformation amount and the deformation position can be measured with greater precision by using the plurality of the amplitudes and phase differences.

Next, the operation of the sensing system according to the present embodiment will be explained. During laparoscopic surgery, as explained previously, the endoscope 7, the electric scalpel, the forceps, and the like are inserted into the interior of the living body 91 through the plurality of holes (for example, the hole 91d) that have been opened in the living body 91. In conjunction with this, the operator 90 inserts the contact detection instrument 1 into the interior of the living body 91 through the hole 91c, starting with the tip base portion 11. While holding the grip portion 13, the operator 90 manipulates the contact detection instrument 1 by moving the grip portion 13 outside of the living body 91, such that the elastic film 10 follows the contour of the internal organ 91b.

Throughout the laparoscopic surgery, the control unit 4 continues to apply voltage to the speaker 14, such that the speaker 14 inputs into the hollow spaces 11b to 11e, 12a, 13a, as the input sound 21, a sine wave at the specified amplitude $A_{in}$ and the specified frequency $f_{in}$.

Thus, when the elastic film 10 is deformed in accordance with the state (the shape, the hardness, and the like) of the internal organ 91b that is being touched, the reflection rate r of the sound within the hollow space changes as a result. For example, if the internal organ 91b that is being touched is comparatively hard tissue such as a lump, the lump presses the elastic film 10 inward into the hollow space, with the result that the path for the sound within the hollow space is narrowed and the reflection rate r of the sound within the hollow space changes. Therefore, the signal that the microphone outputs changes in accordance with the state of the internal organ 91b that is being touched.

Furthermore, the sound is input into the hollow space outside of the living body, and a signal is output outside of the living body in accordance with the sound in the hollow space. Moreover, there are no electronic parts in the rigid tube 12 and the tip base portion 11. Therefore, no electrical signal is generated inside the living body, so the safety of the living body is better than with the known technology. The contact detection instrument 1 can also be sterilized and cleaned easily.

Figure 16:
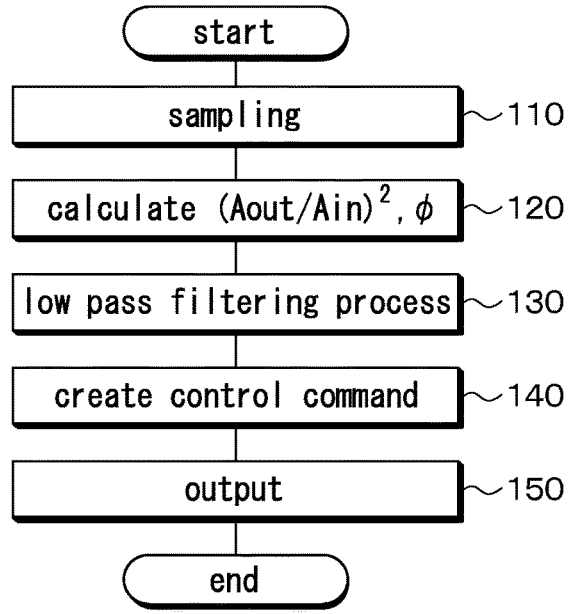
FIG. 16 is a flowchart of processing that a control unit performs.

At the same time that it applies voltage to the speaker 14, the control unit 4 repeatedly performs the processing that is shown in FIG. 16 throughout the laparoscopic surgery. In the processing in FIG. 16, first, at Step 110, sampling is performed to take a specified plurality of samples (for example, 14 samples) of the voltage that is applied to the speaker 14, and sampling is also performed to take a specified plurality of samples (for example, 14 samples) of the signal that is output by the microphone 15 in accordance with the composite sound 24. The voltage that is applied to the speaker 14 corresponds to the intensity of the input sound 21, and the voltage of the signal that is output by the microphone 15 corresponds to the intensity of composite sound 24.

The sampling frequency for the intensities of the input sound 21 and the composite sound 24 is defined as 46,200 Hz, for example, such that 14 samples of the input sound 21 can be taken in each cycle of 3300 Hz. The quantities for the deformation amount and the deformation position are calculated, and a control voltage is output to the haptic presentation device at a sampling frequency of approximately 2300 Hz, based on the deformation amount and the deformation position. Therefore, the input sound and the composite sound are acquired, and the sampling frequency at which the control voltage is transmitted to the haptic presentation device is 2300 Hz. However, taking into account the use of the haptic presentation device 6 and low-pass filter processing with a cut-off frequency of 10 Hz, which will be described later, the sampling frequency at which the control voltage is transmitted may be 1000 Hz or may be 100 Hz. In other words, the sampling frequency needs only to be not less than 100 Hz. However, because human tactile receptors are extremely sensitive to frequencies from zero to 1000 Hz, it is preferable for the sampling frequency to be not less than 1000 Hz. Note that the sampling frequency at which the input sound and the composite sound are sampled requires that the sampling be performed for at least one cycle, so in accordance with the frequency of the input sound, it is necessary to use a sampling frequency of 14 samples per cycle, or more to the extent that it is feasible to do so.

Note that the hollow spaces 11b to 11e, 12a, 13a are sealed by the elastic film 10, the speaker 14, and the microphone 15, so the composite sound 24 is nearly inaudible to a person such as the operator 90 or the like.

Next, at Step 120, the amplitude $A_{in}$ and the phase are computed for the input sound 21, using the intensities of the input sound 21 from the specified plurality of samples that were taken at Step 110 in the current round of the processing in FIG. 16. In the same manner, at Step 120, the amplitude $A_{out}$ and the phase are computed for the composite sound 24, using the intensities of the composite sound 24 from the specified plurality of samples that were taken at Step 110 in the current round of the processing in FIG. 16. Then the difference between the computed phase of input sound 21 and the phase of the composite sound 24 is computed and defined as the phase difference $\phi$. A squared intensity ratio F is then computed using the formula $F=(A_{out}/A_{in})^2$.

Next, at Step 130, the low-pass filter processing with the cut-off frequency of 10 Hz is performed on the squared intensity ratio F and the phase difference $\phi$, using the squared intensity ratio F and the phase difference $\phi$ that were computed at Step 120 in the current and previous rounds of the processing in FIG. 16. The frequency components that exceed 10 Hz are thus removed from the squared intensity ratio F and the phase difference $\phi$.

Next, at Step 140, control commands are created based on the most recent values for the squared intensity ratio F and the phase difference $\phi$, which are the results of the low-pass filter processing that was performed at Step 130 in the current round of the processing in FIG. 16.

The control commands are data that specify the vertical position of each one of the stimulators 65, 66, 67 of the haptic presentation device 6. Here, the vertical position of the first stimulator 65 is defined as H1, the vertical position of the second stimulator 66 is defined as H2, and the vertical position of the third stimulator 67 is defined as H3. H1, H2, and H3 define the positions such that the greater their values, the higher the corresponding stimulators protrude from the body portion 60 against the foot of the operator 90, and when the values are zero, the stimulators do not protrude at all.

The conversion from the squared intensity ratio F and the phase difference $\phi$, to H1, H2, and H3 may be performed as described below, for example. The values $\phi 1$, $\phi 2$, and $\phi 3$ (where $0<\phi 1<\phi 2<\phi 3$) are set as specific values for the phase difference $\phi$. $\phi 1$, $\phi 2$, and $\phi 3$ correspond to the stimulators 65, 66, 67, respectively. Then H1, H2, and H3 are determined by the following formulas:

$$H1=k\times(F-1)/(|\phi-\phi 1|+\alpha)$$

$$H2=k\times(F-1)/(|\phi-\phi 2|+\alpha)$$

$$H3=k\times(F-1)/(|\phi-\phi 3|+\alpha)$$

Here $\alpha$ is a specified positive constant that is set such that H1, H2, and H3 will not become infinitely large, and k is a specified positive proportionality coefficient. The denominator in each formula becomes greater as the respective distances from the phase difference $\phi$ to $\phi 1$, $\phi 2$, and $\phi 3$ become greater. Accordingly, the closer the phase difference $\phi i$ (where i is 1, 2, or 3) is to the phase difference $\phi$, the greater the value of Hi becomes. The value of Hi also becomes greater as the value of F becomes greater.

Alternatively, the conversion from the squared intensity ratio F and the phase difference $\phi$ to H1, H2, and H3 may also be accomplished as described below. Among $\phi 1$, $\phi 2$, and $\phi 3$, if $\phi 1$ is the closest to the phase difference $\phi$, then (H1, H2, H3)=(k×(F−1), 0, 0). If $\phi 2$ is the closest to the phase difference $\phi$, then (H1, H2, H3)=(0, k×(F−1), 0). If $\phi 3$ is the closest to the phase difference $\phi$, then (H1, H2, H3)=(0, 0, k×(F−1)).

In this manner, while a hard lump is in contact with the elastic film 10 as the contact detection instrument 1 is manipulated, the vertical positions H1, H2, and H3 are created by being weighted according to the deformation position xp, which is the position where the lump is in contact with the elastic film 10.

Next, at Step 150, the control commands H1, H2, and H3 that were created at the immediately preceding Step 140 are output to the drive circuit 61 of the haptic presentation device 6 through the cable 5. Thus, as soon as the current round of the processing in FIG. 16 is completed, the next round of the processing in FIG. 16 is started. As has already been explained, the processing in FIG. 16 is performed repeatedly, so the control commands H1, H2, and H3 are output to the drive circuit 61 every time the plurality of the samples are obtained at Step 110.

Note that, in the operation described above, the frequency (the number of times that something happens within a particular period of time) with which the squared intensity ratio F and the phase difference $\phi$ are computed at Step 120 is the same as the frequency (the number of times that something happens within a particular period of time) with which the control commands are output at Steps S140, S150, but both the former and the latter frequency may be changed. For example, when the former frequency is 3300 Hz, the latter frequency may be 2300 Hz, and it may also be 1000 Hz or 100 Hz.

Every time the control commands that have been output from the control unit 4 are acquired, the drive circuit 61 of the haptic presentation device 6 drives the actuators 62, 63, 64 such that the stimulators 65, 66, 67 move to the vertical positions H1, H2, and H3 that the control commands indicate. The stimulators 65, 66, 67 are thus displaced to the vertical positions H1, H2, and H3, respectively. The sole of the foot of the operator 90 thus receives stimuli that correspond to the vertical positions H1, H2, and H3.

Therefore, in a state in which the elastic film 10 is pressed against the internal organ 91b, the manipulating of the contact detection instrument 1 such that it follows the contour of the internal organ 91b makes it possible for the sole of the foot to receive the stimuli that correspond to the deformation amount and the deformation position xp of the elastic film 10 that are generated by the contact between the hard lump and the elastic film 10. More specifically, the tilt of the foot in the front-rear direction varies in accordance with the deformation amount of the elastic film 10, and the tilt of the foot in the left-right direction varies in accordance with the deformation position xp of the elastic film 10.

If the operator 90 then manipulates the contact detection instrument 1 such that the elastic film 10 slowly follows the contour of the internal organ 91b, the amount of deformation that is due to the lump varies along with the deformation position xp, and through the haptic presentation device 6, the operator 90 is able to keep track of the changes in the deformation amount and the changes in position. As a result, the operator 90 is able to detect the presence of the lump with greater precision. In a case where the haptic presentation device 6 conveys to the operator 90 only the stimuli that correspond to the deformation amount, there is a possibility that the operator 90 will not recognize the presence of the lump if he does not move the elastic film 10 promptly, because a human being feels changes in stimuli more sensitively than the stimuli themselves.

In the present embodiment, although sound is utilized, the resonant frequencies of the hollow spaces 11b to 11e, 12a, 13a that result from the deformation of the hollow spaces are not detected, but the intensities Ain, Aout of the input sound 21 and the composite sound 24, and the phase difference $\phi$, are detected. Therefore, scanning and the like of the resonant frequencies is not required, and as a result, the detection speed is faster than in a case where the resonant frequencies are detected. This is extremely effective in the sensing system of the present embodiment, which takes the detected quantities (F, $\phi$) that correspond to the contact between the elastic film 10 and the internal organ 91b and presents them to the operator 90 in close to real time, where a delay that is not less than 0.01 seconds would be a problem. Further, in the present embodiment, only a sound at a specified frequency is used, so the system is strongly resistant to environmental noise.

In the vicinity of the elastic film 10 (that is, in the hollow space 11d), the longitudinal direction 95 of the hollow spaces 11b to 11e, 12a, 13a extends in an arc shape along the circumferential direction 96 of the tip sensor portion 20, such that it encircles the central axis of the tip sensor portion 20. Therefore, in the vicinity of the elastic film 10, the longitudinal direction 95 of the hollow spaces 11b to 11e, 12a, 13a is not orthogonal to the circumferential direction 96 of the tip sensor portion 20. In other words, in the vicinity of the elastic film 10, the hollow spaces 11b to 11e, 12a, 13a extend in the circumferential direction 96 of the tip sensor portion 20.

In the vicinity of the elastic film 10 (that is, in the hollow space 11d), the longitudinal direction 95 of the hollow spaces 11b to 11e, 12a, 13a extends in an arc shape along the circumferential direction 96 of the rigid tube 12, such that it encircles a line that is a direct extension of the central axis of the rigid tube 12. Therefore, in the vicinity of the elastic film 10, the longitudinal direction 95 of the hollow spaces 11b to 11e, 12a, 13a is not orthogonal to the circumferential direction 96 of the rigid tube 12. In other words, in the vicinity of the elastic film 10, the hollow spaces 11b to 11e, 12a, 13a extend in the circumferential direction 96 of the rigid tube 12.

Accordingly, in the vicinity of the elastic film 10 (that is, in the hollow space 11d), the longitudinal direction 95 of the hollow spaces 11b to 11e, 12a, 13a is coincident with a line that is tangent to the movement path 16 of the members 10 to 13. Therefore, in the vicinity of the elastic film 10, the hollow spaces 11b to 11e, 12a, 13a extend in a direction that is tangent to the movement path 16.

Thus, when the operator 90 inserts the contact detection instrument 1 into the living body 91 through the hole 91c and follows the contour of the internal organ 91b with the elastic film 10, if the position of the portion of the elastic film 10 that is in contact with the lump inside the living body 91 changes, the signal that the microphone 15 outputs also changes accordingly. Therefore, the presence of a lump inside the living body can be detected more precisely.

Further, the fact that the haptic presentation device 6 provides the tactile stimuli to the lower body of the operator 90 allows the operator 90 to keep both hands free and also makes it unnecessary for the haptic presentation device 6 to be attached to an arm of the operator 90, which is a sterilized area during the surgery.

Figure 17:
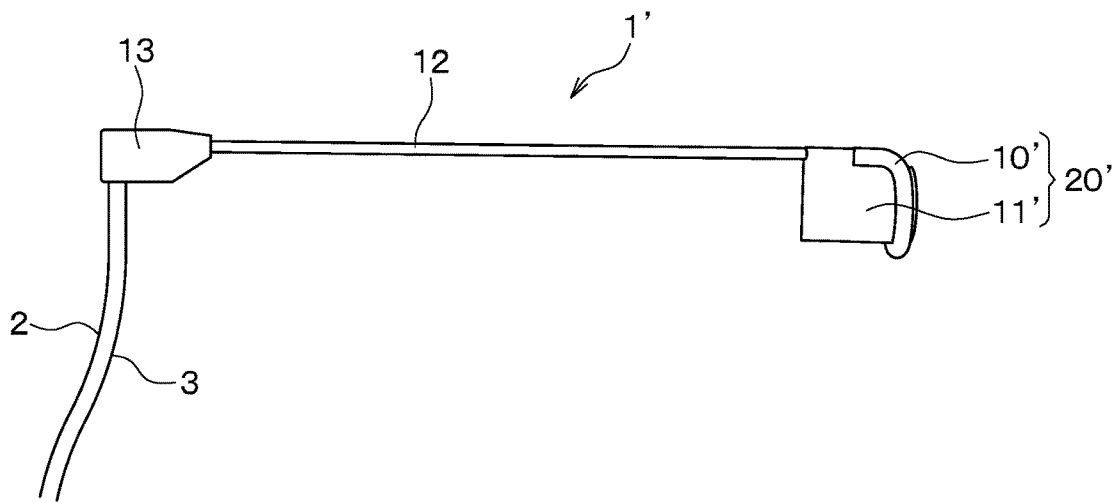
FIG. 17 is a side view of a contact detection instrument 1' that is used for experimentation.
Figure 18:
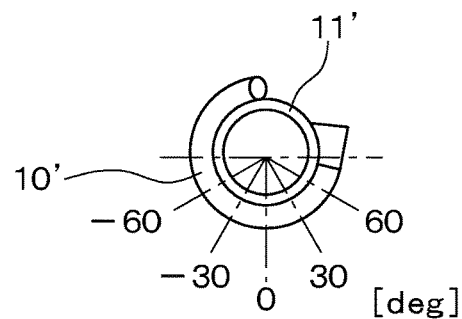
FIG. 18 is a front view of the contact detection instrument 1' that is used for experimentation.

Next, results of experiments conducted by the inventor of the present invention using a contact detection instrument 1' that is similar to the contact detection instrument 1 will be explained. As shown in FIGS. 17 and 18, the contact detection instrument 1' includes the rigid tube 12, the grip portion 13, the speaker 14, and the microphone 15, the same as the contact detection instrument 1. Instead of the tip sensor portion 20, the contact detection instrument 1' includes a tip sensor portion 20'. The tip sensor portion 20' includes a cylindrical elastic tube 10' that is made of silicone rubber and a cylindrical member 11' that is made of ABS resin. The contact detection instrument 1 and the contact detection instrument 1' are the same in being able to detect the deformation position in the circumferential direction of a side face of the tip sensor portion.

The tip of the rigid tube 12 is inserted into one end of the hollow elastic tube 10', which is made of silicone rubber with an outside diameter of 6 millimeters, an inside diameter of 4 millimeters, and a length of 95 millimeters. The other end of the elastic tube 10' is sealed and forms a fixed end.

The elastic tube 10' is wound around the side face of the cylindrical member 11', which has a diameter of 28 millimeters, in the circumferential direction of the cylindrical member 11'. The cylindrical member 11' is attached to the rigid tube 12 such that the axial direction of the cylindrical member 11' is coincident with the longitudinal direction of rigid tube 12.

The deformation position in the circumferential direction of the tip sensor portion 20', the cylindrical member 11', and the rigid tube 12 can thus be known by acquiring the deformation position xp in the longitudinal direction of the elastic tube 10'. The hollow space inside the elastic tube 10', the hollow space 12a, and the hollow space 13a form a single continuous hollow space with a total length of 360 millimeters. The elastic tube 10' covers and seals off the single hollow space, and when the elastic tube 10' is pressed from outside the contact detection instrument 1', the elastic tube 10' is deformed such that it is pressed inward toward the hollow space.

In the vicinity of the elastic tube 10', the longitudinal direction of the hollow space extends along the circumferential direction of the tip sensor portion 20' in an arc shape that encircles the central axis of the tip sensor portion 20'. Therefore, in the vicinity of the elastic tube 10', the longitudinal direction of the hollow space is not orthogonal to the circumferential direction of the tip sensor portion 20'.

In the vicinity of the elastic tube 10', the longitudinal direction of the hollow space extends along the circumferential direction of the of the rigid tube 12, such that it encircles a line that is a direct extension of the central axis of the rigid tube 12. Therefore, in the vicinity of the elastic tube 10', the longitudinal direction of the hollow space is not orthogonal to the circumferential direction of the rigid tube 12.

Therefore, the contact detection instrument 1' is able to demonstrate the same sort of effects as the contact detection instrument 1.

In FIG. 18, positions in the longitudinal direction of the elastic tube 10' are expressed as angles in the circumferential direction of the tip sensor portion 20', the cylindrical member 11', and the rigid tube 12 (the angles being seen from the central axis of the tip sensor portion 20' and the cylindrical member 11'). When the angle is zero degrees, the deformation position xp is disposed 25 millimeters from the tip (the fixed end of the elastic tube 10'), and the input sound 21 that is input from the speaker 14 is a sine wave with a frequency of 3160 Hz. Theoretically, these are experimentally determined design parameters, establishing the condition that at the zero degrees position, the change in the squared intensity ratio $F=(A_{out}/A_{in})^2$ in relation to the deformation amount is at its maximum. The output signal from the microphone 15 is amplified by an amplifier.

The output signal and the voltage signal (the input signal) that is applied to the speaker 14 are input to an oscilloscope, and the phase differences are measured, as recorded in Lissajous figures. The measurements were made when no deformation was applied to the elastic tube 10', as well as when the elastic tube 10' was completely compressed (when r is 1) at −60 degrees, −30 degrees, zero degrees, 30 degrees, and 60 degrees (refer to FIG. 18).

Figure 19:
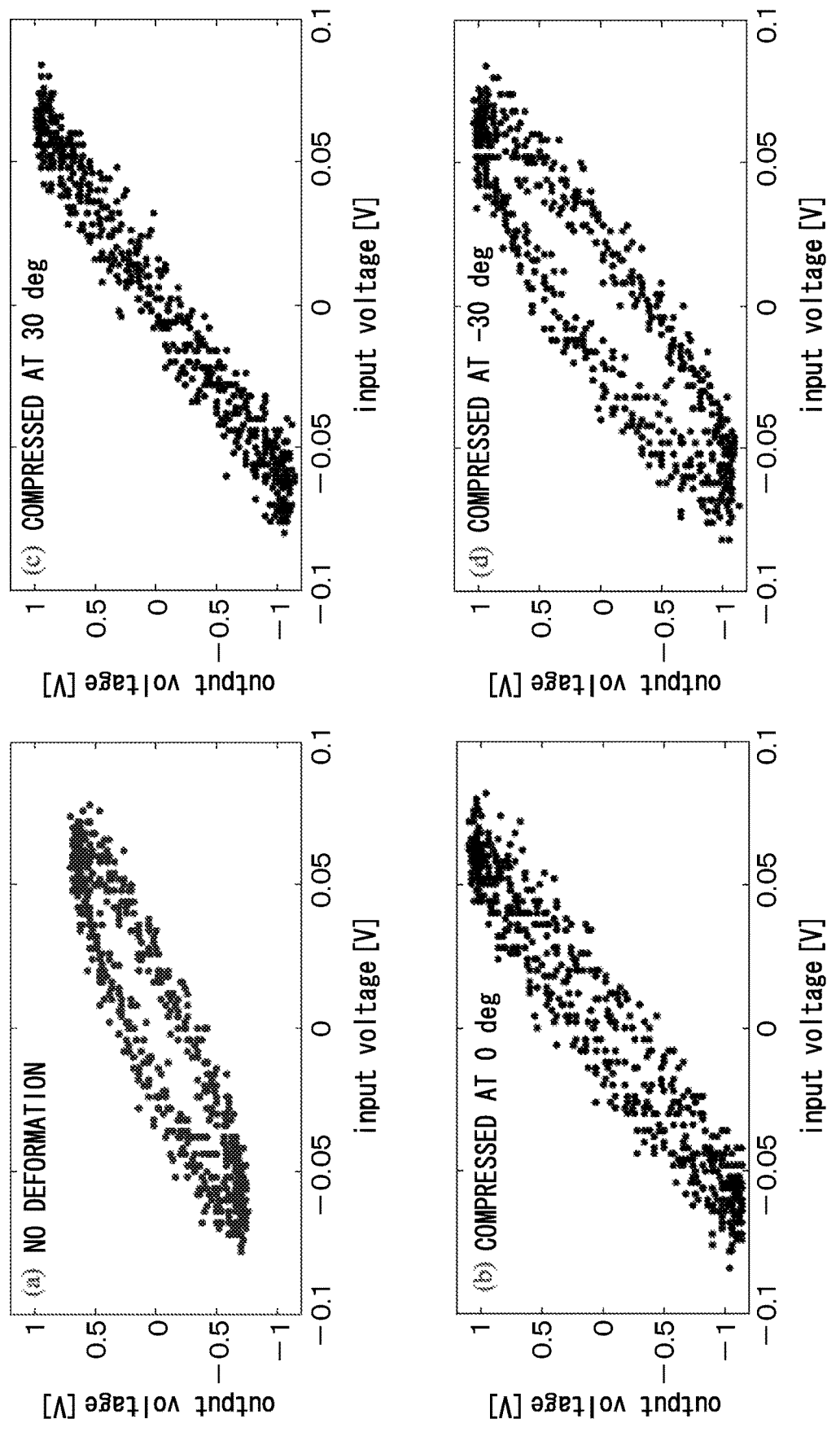
FIG. 19 shows Lissajous figures.
Figure 20:
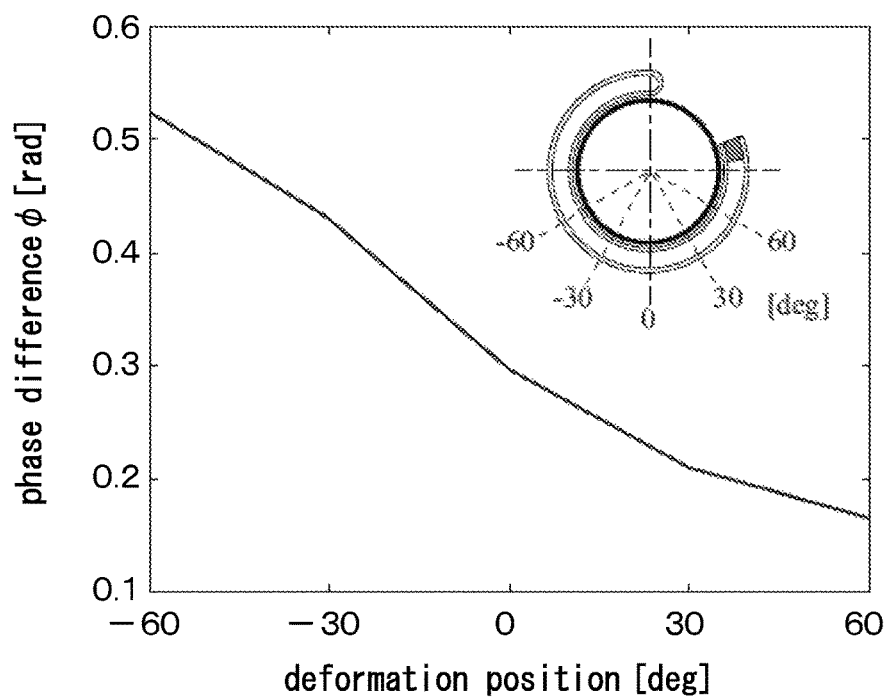
FIG. 20 is a graph that shows the relationship between deformation positions and the phase difference φ.

FIG. 19 shows the Lissajous figures for when no deformation was applied to the elastic tube 10', as well as when the elastic tube 10' was completely compressed at zero degrees, 30 degrees, and −30 degrees. When the figures are compared, it can be seen that the Lissajous figures vary in correspondence with the deformation position. Comparing the figure for when deformation was not applied to the figures for when deformation was applied, the amplitude of the voltage of the output signal becomes greater, and this indicates that the amplitude corresponds to the deformation amount. The phase differences φ in relation to the various deformation positions are shown in FIG. 20. It can be seen from FIG. 20 that the phase difference φ varies according to the deformation position of the elastic tube 10'. These results indicate that even in a state in which the elastic tube 10' is wound around the cylindrical member 11', the deformation position xp can be acquired by measuring the phase difference φ.

Note that the contact detection instrument 1' that was used in the experiments can also be used in the sensing system instead of the contact detection instrument 1. In that case, the contact detection instrument 1' will be easier to insert into the living body 91 if the diameter of the cylindrical member 11' is made smaller than 28 millimeters.

(Second Embodiment)

Figure 21:
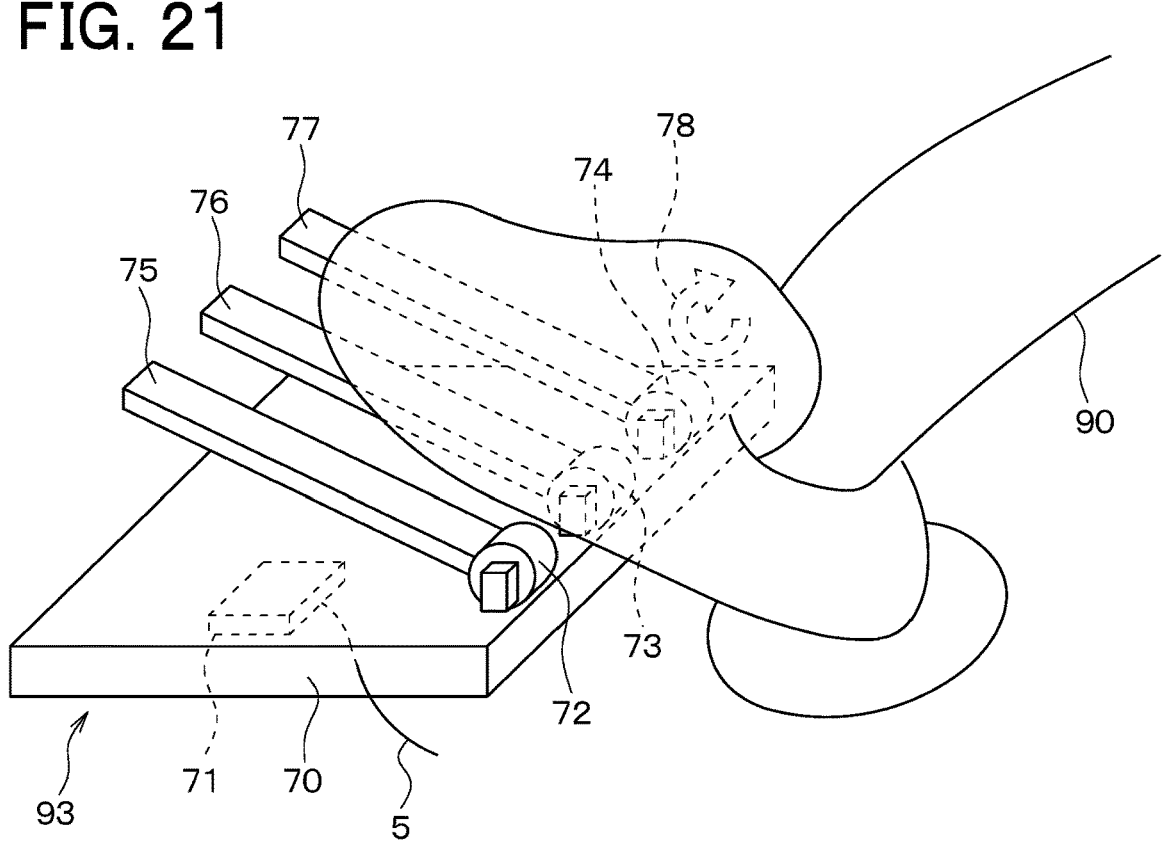
FIG. 21 is a configuration diagram of a haptic presentation device 93 according to a second embodiment.

Next, a second embodiment of the present invention will be explained. In the second embodiment, the haptic presentation device 6 of the first embodiment is replaced by a haptic presentation device 93 that is shown in FIG. 21. Except for the haptic presentation device 93, the configuration and operation of the second embodiment are the same as in the first embodiment.

As shown in FIG. 21, the haptic presentation device 93 includes a body portion 70, which is placed on the floor, a drive circuit 71, which is disposed in the interior of the body portion 70, and three actuators 72, 73, 74, which are connected to the drive circuit 71. The haptic presentation device 93 also includes three stimulators 75, 76, 77, which are displaced by being driven by the actuators 72, 73, 74, respectively, the displacing of the stimulators 75, 76, 77 serving to provide tactile stimuli to the sole of the foot of the operator 90.

The drive circuit 71 drives the actuators 72 to 74 in accordance with the control commands that are output from the control unit 4 through the cable 5.

The actuators 72 to 74 are attached to the body portion 70, each having a rotation portion that is able to rotate in relation to the body portion 70 as indicated by the arrow 78. The stimulators 75, 76, 77 are each a long, narrow flat plate, one end of which is secured to the rotation portion of the corresponding one of the actuators 72, 73, 74. By rotating their rotation portions in relation to the body portion 70 in accordance with the driving of the drive circuit 71, the actuators 72 to 74 change the positions and orientations of the stimulators 75, 76, 77. Specifically, the stimulators 75, 76, 77 are displaced by pivoting around the actuators 72, 73, 74, respectively.

As shown in FIG. 21, the operator 90 keeps his heel on the floor and places only the front portion of his foot on the top faces of the stimulators 75 to 77. Therefore, when the positions and orientations of the stimulators 75 to 77 change by pivoting around the actuators 72 to 74, respectively, the operator 90 recognizes the changes in the tactile stimuli on the front end portion of the sole of the foot.

Next, the operation of the haptic presentation device 93 will be explained. Every time the control commands that have been output from the control unit 4 are acquired, the drive circuit 71 of the haptic presentation device 93 drives the actuators 72, 73, 74 such that the stimulators 75, 76, 77 move to the corresponding vertical positions H1, H2, H3 that are indicated by the control commands.

Specifically, if the vertical position H1 is zero, the actuator 72 is controlled such that the stimulator 75 becomes parallel to the floor, and as the vertical position H1 becomes greater, the actuator 72 is controlled such that the angle of elevation of the stimulator 75 above the floor becomes greater, and the position of the end of the stimulator 75 that is not secured to the actuator 72 becomes higher. The relationship of the vertical position H2, the actuator 73, and the stimulator 76 and the relationship of the vertical position H3, the actuator 74, and the stimulator 77 are the same. In this manner, the sole of the foot of the operator 90 receives the tactile stimuli that correspond to the vertical positions H1, H2, and H3.

Therefore, in a state in which the elastic film 10 is pressed against the internal organ 91b, the manipulating of the contact detection instrument 1 such that it follows the contour of the internal organ 91b makes it possible for the sole of the foot to receive the stimuli that correspond to the deformation amount and the deformation position xp of the elastic film 10 that are generated by the contact between the hard lump and the elastic film 10. More specifically, the tilt of the foot in the front-rear direction varies in accordance with the deformation amount of the elastic film 10, and the tilt of the foot in the left-right direction varies in accordance with the deformation position xp of the elastic film 10. Therefore, effects are achieved that are equivalent to those of the haptic presentation device 6 in the first embodiment. Furthermore, the heel of the foot becomes a fixed base point, making it possible for the operator 90 to perceive the movement of his own foot more easily.

(Third Embodiment)

Figure 22:
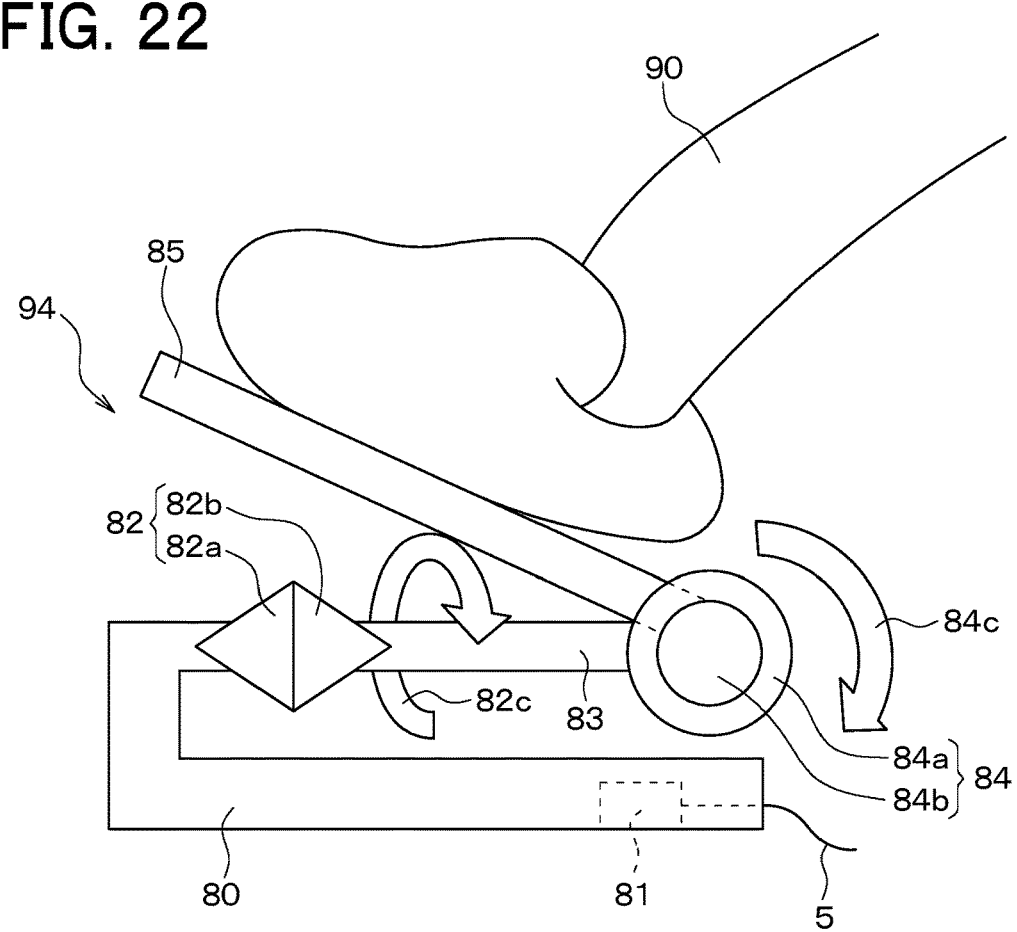
FIG. 22 is a configuration diagram of a haptic presentation device 94 according to a third embodiment.

Next, a third embodiment of the present invention will be explained. In the third embodiment, the haptic presentation device 6 of the first embodiment is replaced by a haptic presentation device 94 that is shown in FIG. 22. The content of the control commands that the control unit 4 outputs to the haptic presentation device 94 is also different from what it is in the first embodiment. The configuration and operation of the third embodiment are otherwise the same as in the first embodiment.

As shown in FIG. 22, the haptic presentation device 94 includes a body portion 80, which is placed on the floor, a drive circuit 81, which is disposed in the interior of the body portion 80, and two actuators 82, 84, which are connected to the drive circuit 81. The haptic presentation device 94 also includes a shaft 83 and a stimulator 85, and tactile stimuli are provided to the sole of the foot of the operator 90 by driving the actuators 82, 84 such that the shaft 83 and the stimulator 85 are displaced.

The drive circuit 81 drives the actuators 82, 84 in accordance with the control commands that are output from the control unit 4 through the cable 5.

The actuator 82 includes a fixed portion 82a, which is secured to the body portion 80, and a rotation portion 82b, which is able to rotate in relation to the fixed portion 82a. The rotation portion 82b is driven by the drive circuit 81 such that it rotates in relation to the fixed portion 82a in the direction of the arrow 82c. The shaft 83 is a member with one end affixed to the rotation portion 82b of the actuator 82 and the other end affixed to the actuator 84.

The actuator 84 includes a fixed portion 84a, to which the other end of the shaft 83 is affixed, and a rotation portion 84b, which is able to rotate in relation to the fixed portion 84a. The rotation portion 84b is driven by the drive circuit 81 such that it rotates in relation to the fixed portion 84a in the direction of the arrow 84c. The stimulator 85 is a long, narrow flat plate, one end of which is secured to the rotation portion 84b of the actuator 84.

When the rotation portion 82b of the actuator 82 rotates in relation to the fixed portion 82a, the shaft 83, the actuator 84, and the stimulator 85 also rotate in conjunction around the actuator 82 as the center of rotation. When the rotation portion 84b of the actuator 84 rotates in relation to the fixed portion 84a, the stimulator 85 also rotates in conjunction around the actuator 84 as the center of rotation. The stimulator 85 rotates in a different direction when the rotation portion 82b rotates than it does when the rotation portion 84b rotates, so the stimulator 85 is displaced with two degrees of freedom.

As shown in FIG. 22, the operator 90 places his entire foot on the top face of the stimulator 85. Accordingly, when the position and the orientation of the stimulator 85 change in relation to the centers of rotation of the actuators 82, 84, the operator 90 recognizes the changes in the tactile stimuli to the front end portion of the sole of the foot. Specifically, when the actuator 82 is driven, the tilt of the foot on the stimulator 85 changes in the left-right direction, and when the actuator 84 is driven, the tilt of the foot on the stimulator 85 changes in the front-rear direction.

Next, the control commands that the control unit 4 outputs to the haptic presentation device 94 through the cable 5 will be explained. At Steps S110 to S130 in FIG. 16, the control unit 4 performs the same operations as in the first embodiment.

At Step 140, in the same manner as in the first embodiment, the control commands are created based on the most recent values for the squared intensity ratio F and the phase difference $\phi$, which are the results of the low-pass filter processing that was performed at Step 130 in the current round of the processing in FIG. 16. However, the content of the control commands is different from the content in the first embodiment.

The control commands in the present embodiment are data that specify a tilt $\theta 1$ in the left-right direction and a tilt $\theta 2$ in the front-rear direction for the foot that is placed on the stimulator 85 of the haptic presentation device 94. As the value of the tilt $\theta 2$ becomes greater, the height of the toes of the foot becomes greater.

The conversion from the squared intensity ratio F and the phase difference $\phi$ to the tilts $\theta 1$, $\theta 2$ may be performed as hereinafter described, for example. First, the value of the tilt $\theta 2$ may be increased as the value of the squared intensity ratio F increases, without being dependent on the value of the phase difference $\phi$. The value of the tilt $\theta 1$ may be increased as the value of the phase difference $\phi$ increases, without being dependent on the value of the squared intensity ratio F.

Next, at Step 150, the control commands $\theta 1$, $\theta 2$ that were created at the immediately preceding Step 140 are output to the drive circuit 81 of the haptic presentation device 94 through the cable 5. Every time the control commands that have been output from the control unit 4 are acquired, the drive circuit 81 drives the actuator 82 such that the tilt angle $\theta 1$ specified by the control command is implemented and drives the actuator 24 such that the tilt angle $\theta 2$ specified by the control command is implemented. The sole of the foot of the operator 90 thus receives the tactile stimuli that correspond to the tilt angles $\theta 1$, $\theta 2$.

Therefore, in a state in which the elastic film 10 is pressed against the internal organ 91b, the manipulating of the contact detection instrument 1 such that it follows the contour of the internal organ 91b makes it possible for the sole of the foot to receive the stimuli that correspond to the deformation amount and the deformation position xp of the elastic film 10 that are generated by the contact between the hard lump and the elastic film 10. More specifically, the tilt of the foot in the front-rear direction varies in accordance with the deformation amount of the elastic film 10, and the tilt of the foot in the left-right direction varies in accordance with the deformation position xp of the elastic film 10. Therefore, effects are achieved that are equivalent to those of the haptic presentation device 6 in the first embodiment.

(Fourth embodiment)

Figure 23:
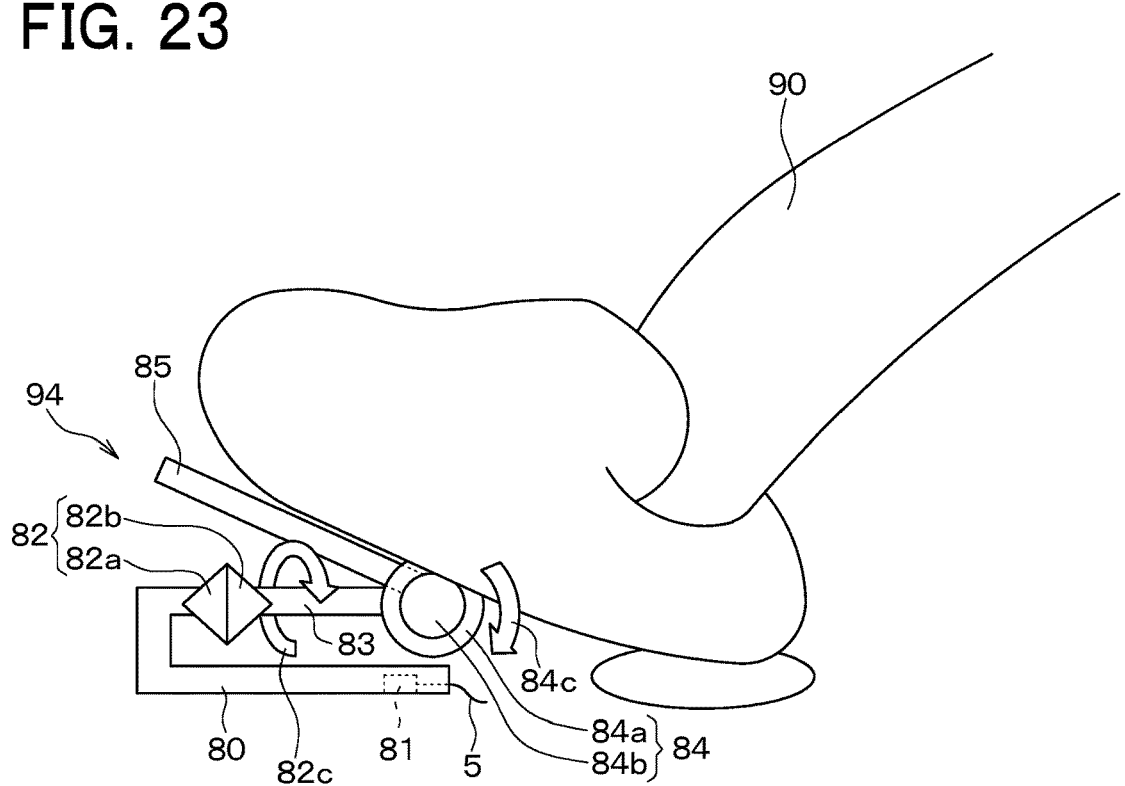
FIG. 23 is a configuration diagram of the haptic presentation device 94 according to a fourth embodiment.

Next, a fourth embodiment of the present invention will be explained. In the fourth embodiment, the size of the haptic presentation device 94 is smaller than in the third embodiment, but the fourth embodiment is otherwise the same as the third embodiment. As shown in FIG. 23, in the present embodiment, the operator 90 rests his heel on the floor and places only the front portion of his foot on the top face of the stimulator 85. Therefore, the heel of the foot becomes a fixed base point, making it possible for the operator 90 to perceive the movement of his own foot more easily.

(Fifth Embodiment)

Next, a fifth embodiment of the present invention will be explained with reference to FIGS. 24 to 34. In the fifth embodiment, the tip sensor portion 20 in the first to the fourth embodiments is replaced by a tip sensor portion 20". Except for the tip sensor portion, the configuration is the same as in the first to the fourth embodiments.

The tip sensor portion 20" is configured from an elastic film 10" and a tip base portion 11". The material of the tip base portion 11" is the same as that of the tip base portion 11. The tip base portion 11" extends almost straight in the same direction as the longitudinal direction of the rigid tube 12, but it has a moderately arced shape like that of a forceps. The outside diameter of the tip base portion 11" is 7 millimeters, for example, giving it a width that can be passed through the hole 91c. The length of the tip base portion 11" in the longitudinal direction is 70 millimeters, for example.

Figure 24:
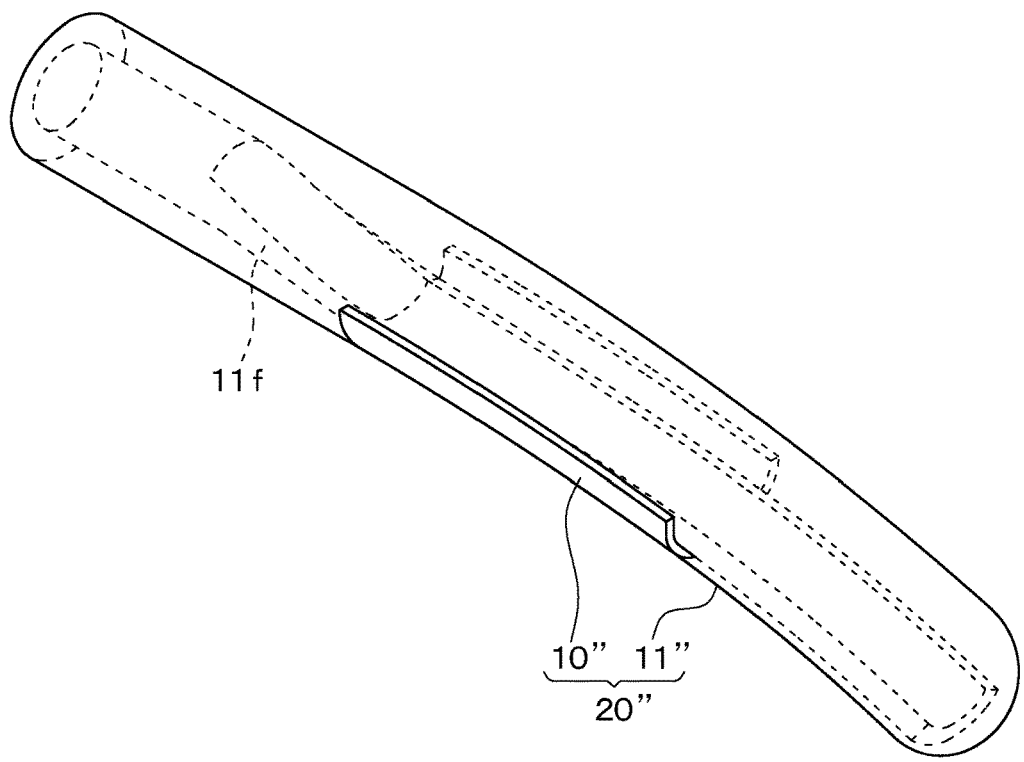
FIG. 24 is an oblique view of a tip sensor portion 20" according to a fifth embodiment.
Figure 25:
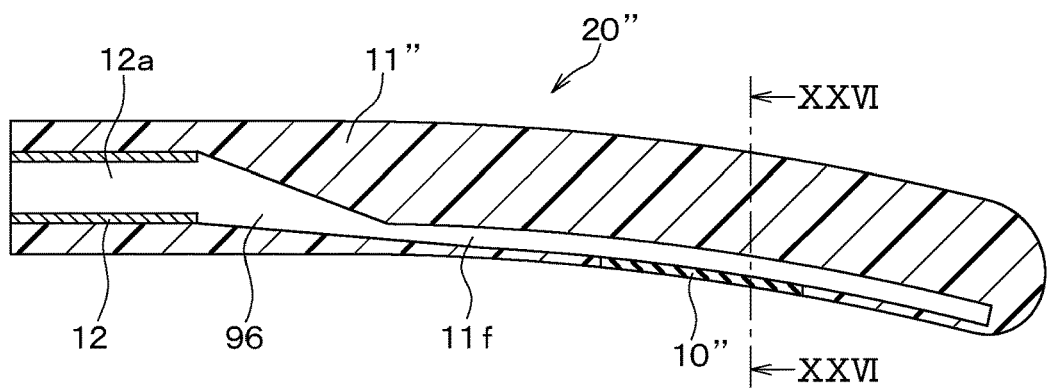
FIG. 25 is a longitudinal section view of the tip sensor portion 20".
Figure 26:
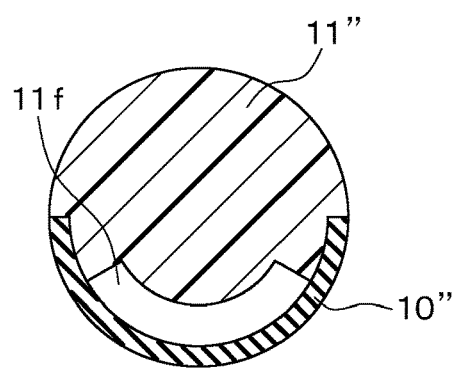
FIG. 26 is a section view at the line XXVI-XXVI in FIG. 25.

As shown in FIGS. 24 to 26, a hollow space 11f is formed in the interior of the tip base portion 11". The hollow space 11f has an opening at the rigid tube 12 end of the tip base portion 11". One end of the rigid tube 12 is inserted into the opening, making the hollow space 11f continuous with the hollow space 12a.

In the vicinity of the opening, the hollow space 11f has a cylindrical shape, but the cross-sectional shape of the hollow space 11f changes as one moves toward the tip end (the opposite end from the rigid tube 12), becoming arc-shaped in cross section, as shown in FIG. 26. The elastic film 10" is attached to the tip base portion 11" such that it covers and seals off the portion of the hollow space 11f that is arc-shaped in cross section. The material and the shape of the elastic film 10" are the same as those of the elastic film 10 in the first embodiment. When the elastic film 10" is pressed from outside the contact detection instrument 1, the elastic film 10" is deformed such that it is pressed inward toward the hollow space 11f.

The significance of the shape of hollow space 11f will be explained. A lump is something that is caused by a change in hardness or shape that is due a pathological change in a portion of a normal part of the internal organ 91b, and because the normal part is soft, it is conceivable that the force that bears on the elastic film 10" when the tip sensor portion 20" follows the contour of a lump will be similar to the force when the tip sensor portion 20" follows the contour of a minute irregularity. When the tip sensor portion 20" passes over an irregularity, it is subject to forces in the normal direction and a tangential direction, with the angle of the force in the normal direction varying according to the position. The hollow space 11f, which is a path for the sound, is narrowed mainly by the force in the normal direction. It is therefore desirable for the portion of the hollow space 11f that is deformed to be deformed irrespective of the angle of the force in the normal direction. Furthermore, the way in which the hollow space narrows improves the sensitivity to the amount by which the lump presses on the elastic film 10". Accordingly, the hollow space 11f is structured to have the arc-shaped space that is shown in FIG. 26, such that even as the hollow space narrows, it is able to respond to changes in the direction of the force.

The longitudinal direction of the hollow space 11f is the same as the longitudinal direction of the tip base portion 11" and it orthogonal to the circumferential direction of the tip sensor portion 20". Therefore, in the present embodiment, the direction in which the elastic film 10" follows the contour of the internal organ 91b is orthogonal to the longitudinal direction of the hollow space 11f.

Next, the operation of the present embodiment will be explained, covering only the differences from the first to the fourth embodiments. In the present embodiment, at Step 140, the control unit 4 creates the control commands (that is, the combination of H1, H2, H3, or the combination of θ1, θ2) based on only one of the squared intensity ratio F and the phase difference ϕ.

For example, in a case where the control commands that include H1, H2, H3 are created, the control commands may be created such that H1, H2, H3 are all defined as having the same value, with the value of H1, H2, H3 becoming greater as the squared intensity ratio F becomes greater. Alternatively, the control commands may be created such that the value of H1, H2, H3 becomes greater as the phase difference ϕ becomes greater.

To take another example, in a case where the control commands that include θ1, θ2 are created, the control commands may be created such that the value of θ1 is fixed at zero, with the value of θ2 becoming greater as the squared intensity ratio F becomes greater. Alternatively, the control commands may be created such that the value of θ1 is fixed at zero, with the value of θ2 becoming greater as the phase difference ϕ becomes greater.

In both of these cases, the control commands that are output from the control unit 4 to the haptic presentation device 6 indicate quantities with one degree of freedom based on the squared intensity ratio F or quantities with one degree of freedom based on the phase difference ϕ. Alternatively, the control commands may also indicate quantities with one degree of freedom based on both the squared intensity ratio F and the phase difference ϕ.

Thus, when the operator 90 inserts the contact detection instrument 1 of the present embodiment into the living body 91 through the hole 91c and follows the contour of the internal organ 91b with the elastic film 10", if the elastic film 10" is deformed by coming into contact with a lump inside the living body 91, the signal that the microphone 15 outputs also changes accordingly. Therefore, the presence of a lump inside the living body can be detected.

Figure 27:
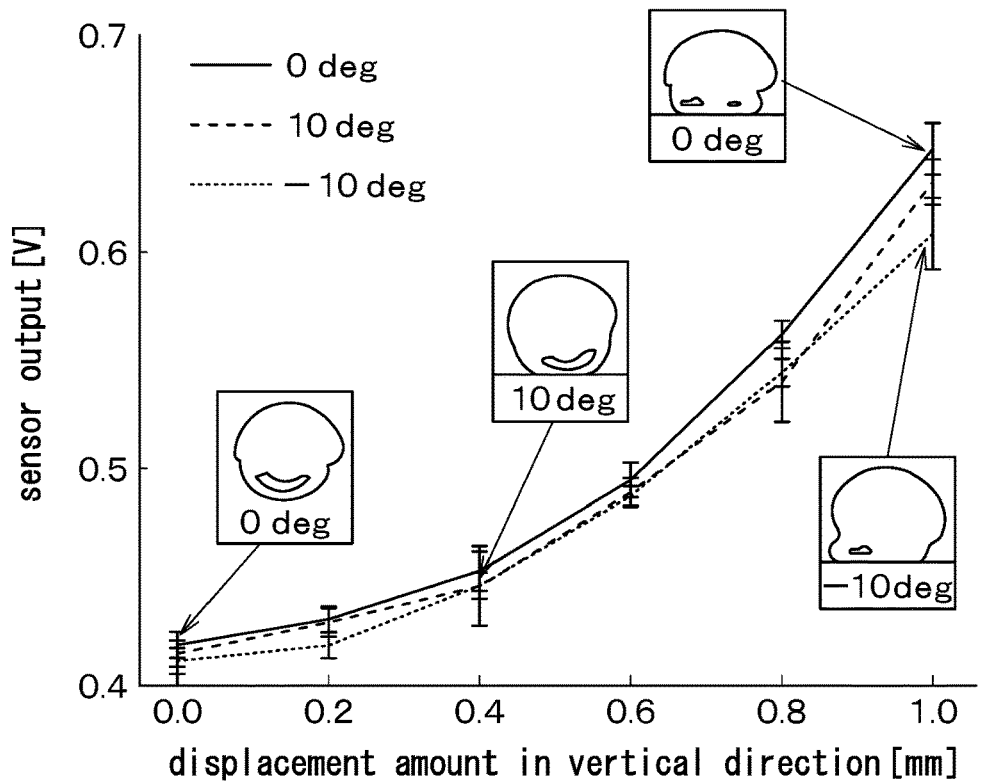
FIG. 27 is a figure that shows experimental results for the fifth embodiment.

Next, a basic experiment was conducted using the improved sensor. Displacement was imposed on the elastic film 10", and the sound pressure level in the single hollow space 11f, 12a, 13a was measured in relation to the displacement, at the input frequency (3080 Hz in the current experiment) of the input sound 21. A 5-millimeter square acrylic plate was used as the object that pressed against the elastic film 10", substituting for the lump in question. Note that, in order to confirm that the normal direction force on the surface of the lump could be detected, the same experiment was conducted with the tip sensor portion 20" rotated ±10 degrees, with the longitudinal direction of tip sensor portion 20" serving as the axis of rotation. The results are shown in FIG. 27. The figure shows states of cross-sectional deformation that were photographed using a cut model. According to FIG. 27, it can be seen that the squared intensity ratio F changes in accordance with the change in the amount of displacement. Therefore, in a case where the control commands that correspond to the squared intensity ratio F are output to the haptic presentation device 6, the tactile stimuli that are provided by the haptic presentation device 6 enable the operator 90 to perceive the displacement of the elastic film 10" by the lump.

Figure 28:
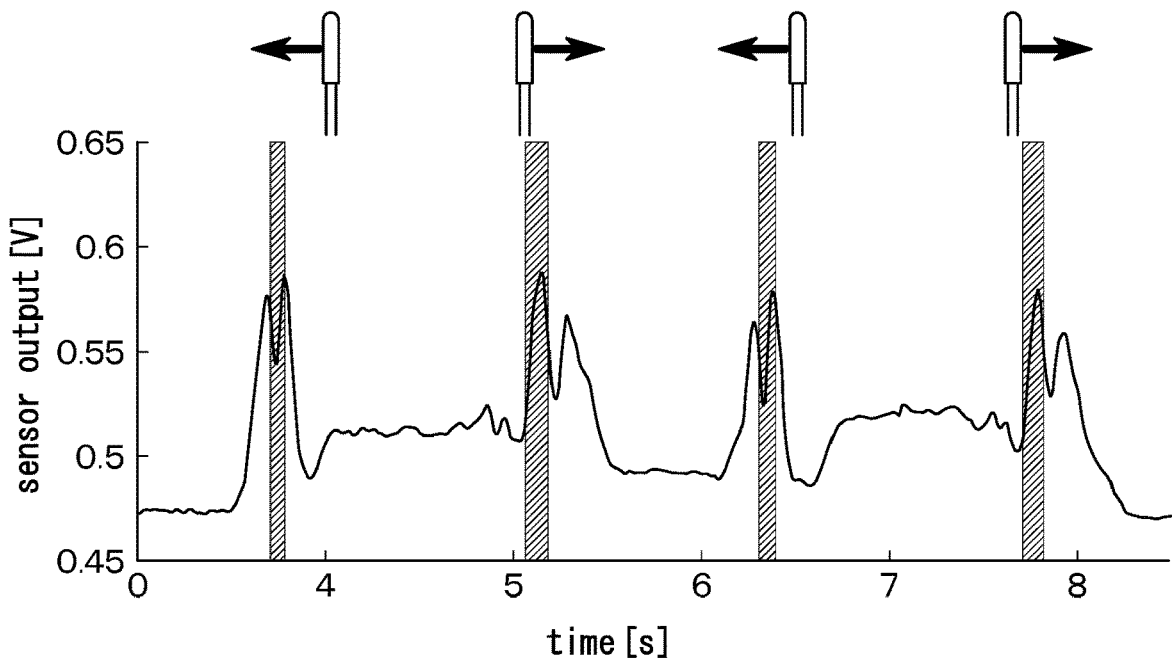
FIG. 28 is a figure that shows experimental results for the fifth embodiment.

A contour-following test was also conducted using the improved sensor on a simulated lump. The lump has a diameter of 15 millimeters, and the portion outside the lump has folds that simulate an intestine. In the experiment, the actual conditions were emulated, and the contour-following test was conducted starting from the underside surface of the lump and the folds. FIG. 28 shows the sound pressure levels inside the pipe when the contour of the simulated lump was followed four times. The shaded areas in the figure indicate the position of the lump, and schematic drawings indicating the directions of the contour-following operations are also shown. According to this figure, it can be seen that a squared intensity ratio that corresponds to the lump could be obtained.

Figure 29:
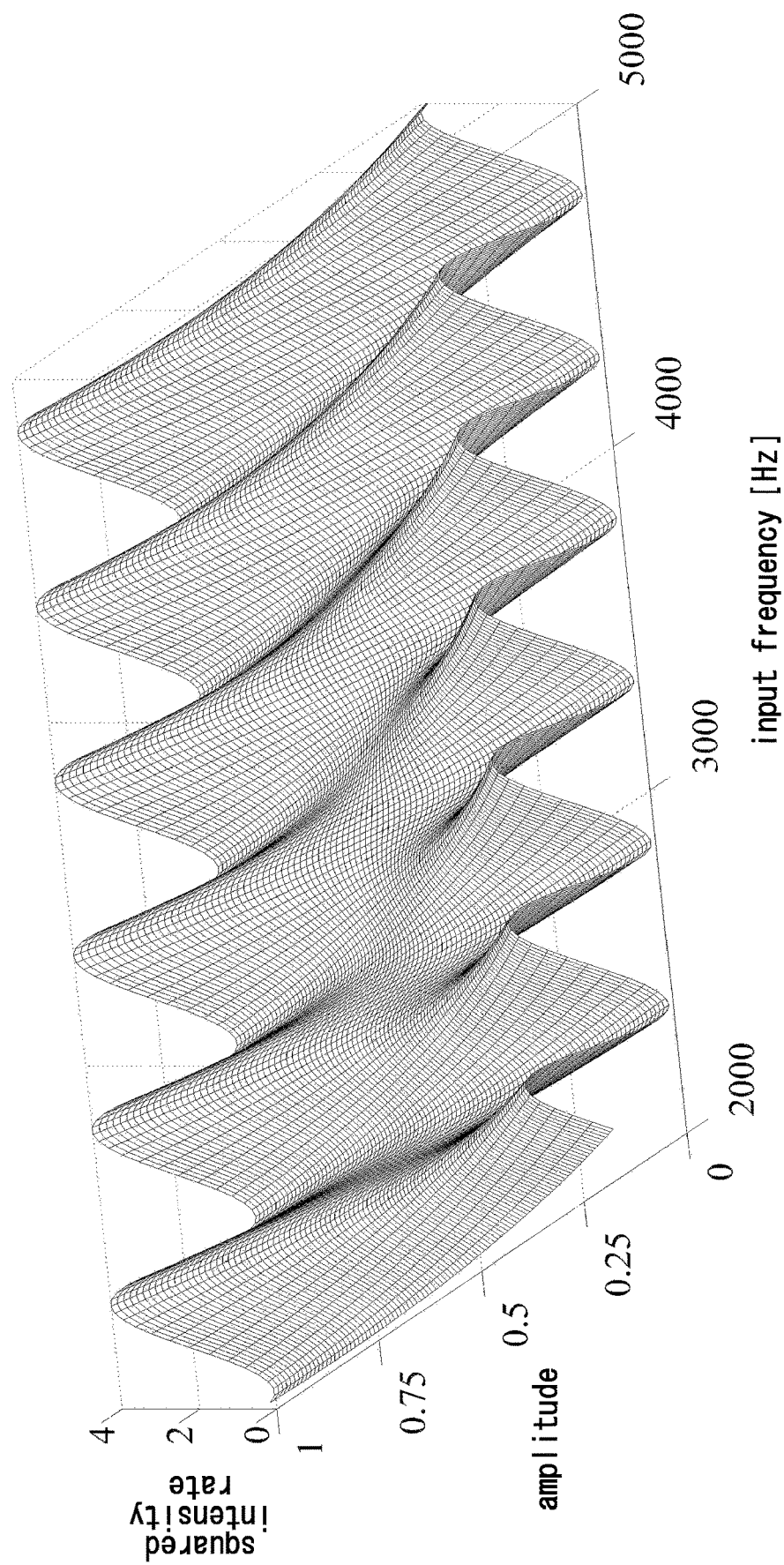
FIG. 29 is a figure that shows a squared intensity ratio F in relation to the reflection rate r and an input frequency $f_{in}$.

Note that, in Equations (1) to (3), L was defined as 360 millimeters, v was defined as 340 meters/second, and xp was defined as 25 millimeters, and the results of calculating the squared intensity ratio F in relation to the deformation amount (the reflection rate r) and the input frequency $f_{in}$ are as shown in FIG. 29. According to the figure, it can be seen that the change in the squared intensity ratio F in relation to the change in the reflection rate r becomes especially noticeable when the input frequency $f_{in}$ is around 3300 Hz. Therefore, if the input frequency $f_{in}$ is set appropriately, the contact detection instrument 1 is effective as a sensor.

Figure 30:
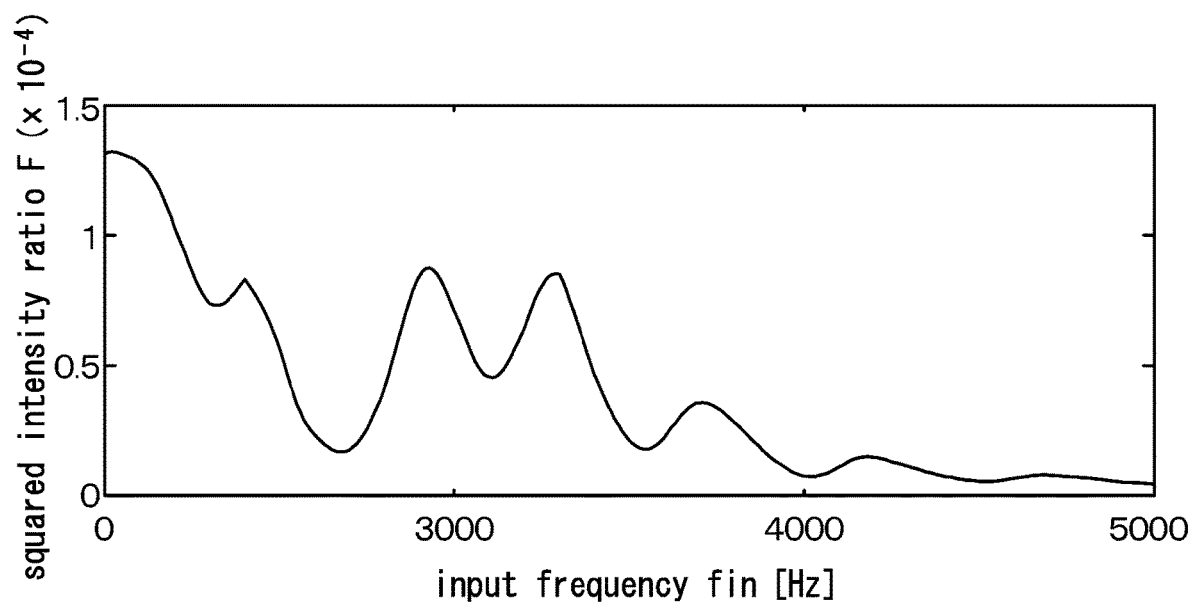
FIG. 30 is a figure that shows experimental results for the fifth embodiment.

In FIG. 29, the theoretical value of the resonance property of the contact detection instrument 1 is indicated in the area where the reflection rate r is zero. Results of the measurement of the resonance property of the contact detection instrument 1 of the present embodiment are shown in FIG. 30. When FIGS. 29 and 30 are compared, it can be seen that the intervals between the peaks and troughs match almost perfectly. However, in FIG. 30, the sound pressure decreases in the region where the frequency is low and the region where it is high. This is thought to be due to absorption of the sound. Therefore, the input frequency $f_{in}$ was set to 3080 Hz to avoid the occurrence of sound absorption. From the same standpoint, any frequency from 2500 Hz to 4000 Hz can be used.

What is output to the haptic presentation device 6 of the present embodiment is one of a quantity that corresponds to the squared intensity ratio F and a quantity that corresponds to the phase difference ϕ, and as can be understood from Equations (2) and (3), the deformation amount is derived regardless of which quantity is used. Accordingly, Equations (1) to (3) are used to perform a theoretical analysis of the two sensor outputs of the squared intensity ratio F and the phase difference ϕ, with the squared intensity ratio F defined as Ea and the phase difference ϕ, defined as Ep.

First, the evaluation standards will be explained. If the parameters $f_{in}$, xp, L and v are fixed, each sensor output Ei (where i={a, p}) is a function of the reflection rate r. Therefore, if the parameters are designed appropriately, the sensor will detect the deformation amount (the reflection rate r). If the sound velocity v within the hollow spaces and the total length L of the hollow spaces in the longitudinal direction are treated as constants, the input frequency $f_{in}$ and the deformation position xp become the only remaining design parameters. If the combination of these two parameters is set appropriately, the sensor will be effective. In setting the design parameters, it is necessary to evaluate the sensor output. What is desirable for the sensor output is for the range of the sensor output to be wide in relation to changes in the reflection rate r and for it to have good linearity. Note that the reflection rate r was posited to change linearly in relation to pressure deformation. First, the difference Si between the maximum value and the minimum value of the sensor output was adopted as the value to be used for evaluating the output range. The difference Si is expressed by Equation (4) below.

[Formula 3]

$$Si = \max_{0 \leq r \leq 1} Ei - \min_{0 \leq r \leq 1} Ei \quad (4)$$

Next, a correlation coefficient Ri for the correlation between the reflection rate r and each sensor output Ei was adopted as the value to be used for evaluating the linearity. The correlation coefficient Ri is expressed by Equation (5) below.

[Formula 4]

$$Ri = \frac{\int_0^1 (r - \bar{r})(Ei - \overline{Ei})\,dr}{\sqrt{\int_0^1 (r - \bar{r})^2\,dr \int_0^1 (Ei - \overline{Ei})^2\,dr}} \quad (5)$$

The linearity of the sensor output becomes better as the value of Ri approaches ±1.

The analysis was conducted using the two evaluation values described above. Note that for the analysis, v was set to 340 meters/second, and L was set to 0.36 meters.

Figure 31:
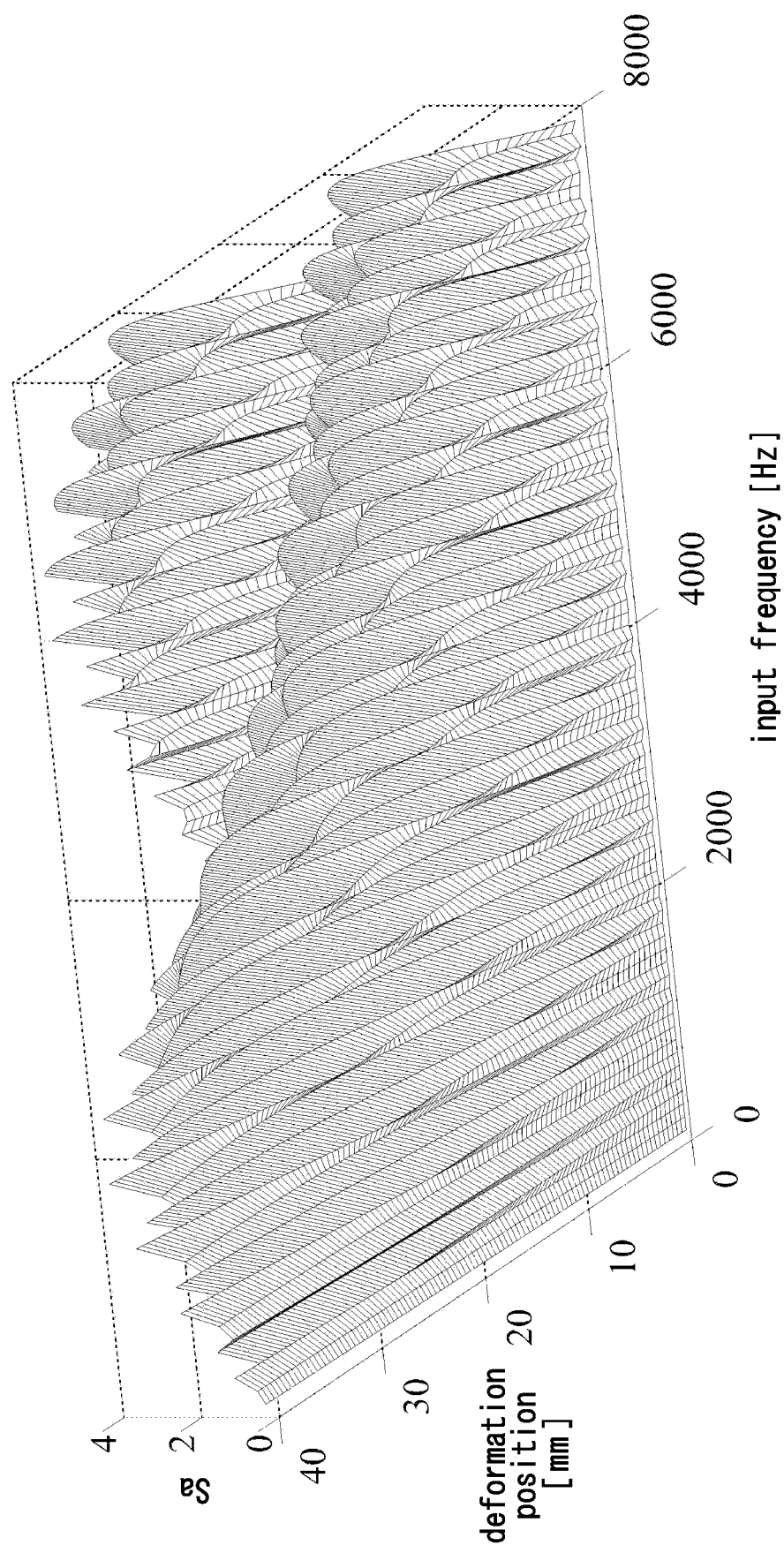
FIG. 31 is a figure that shows the value of a value Sa in accordance with the input frequency $f_{in}$ and the deformation position xp.
Figure 32:
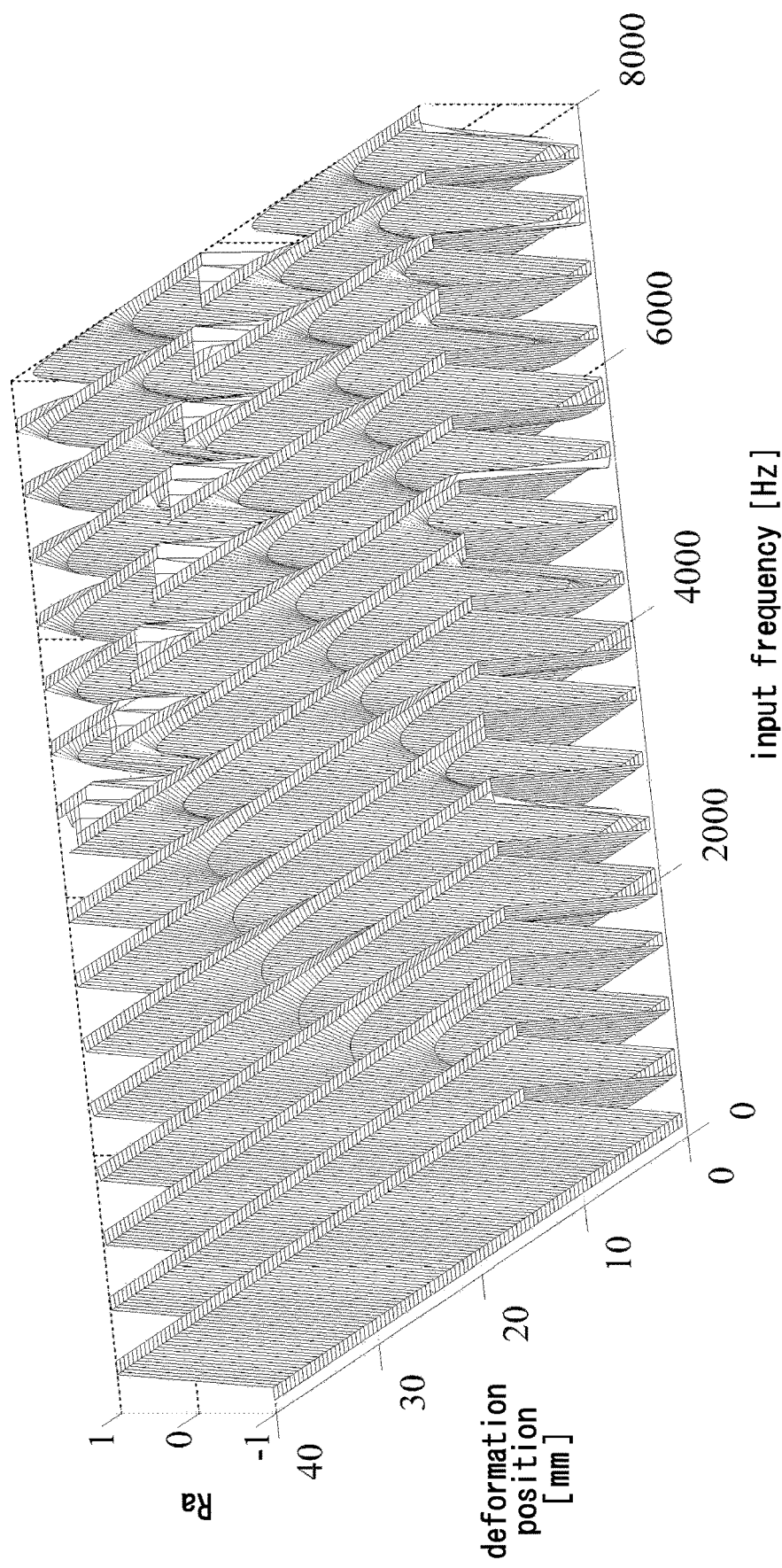
FIG. 32 is a figure that shows the value of a value Ra in accordance with the input frequency $f_{in}$ and the deformation position xp.

First, the results of the analysis when Ea is used as the sensor output will be explained. FIG. 31 shows the value of Sa that is calculated by Equation (4) in relation to each combination of the design parameters ($f_{in}$, xp). In FIG. 31, it is preferable for a combination ($f_{in}$, xp) to be used for which the value of Sa is high. FIG. 31 also shows that changes in the sensor output are dependent on both $f_{in}$ and xp. In particular, in the range where the value of $f_{in}$ is large, it can be seen that the sensor output changes readily in relation to xp. Next, FIG. 32 shows the value of Ra that is calculated by Equation (5) in relation to the combination ($f_{in}$, xp). FIG. 32 shows that when Ra is positive, the linearity of the sensor output becomes better as the value of Ra approaches 1. Even when Ra is negative, the slope simply becomes negative, and the linearity of the sensor output becomes better as the value of Ra approaches −1. On the other hand, in the region where the absolute value of Ra is close to zero (for example, the region where the absolute value of Ra is not greater than 0.1), FIG. 32 shows that the linearity is poor, so that region must be avoided. FIG. 32 thus shows that the linearity is good for almost all combinations of ($f_{in}$, xp). Therefore, in a case where the control commands that correspond to the squared intensity ratio F are output to the haptic presentation device 6, the tactile stimuli that are provided by the haptic presentation device 6 make it possible for the operator 90 to perceive the displacement of the elastic film 10″ by the lump.

Figure 33:
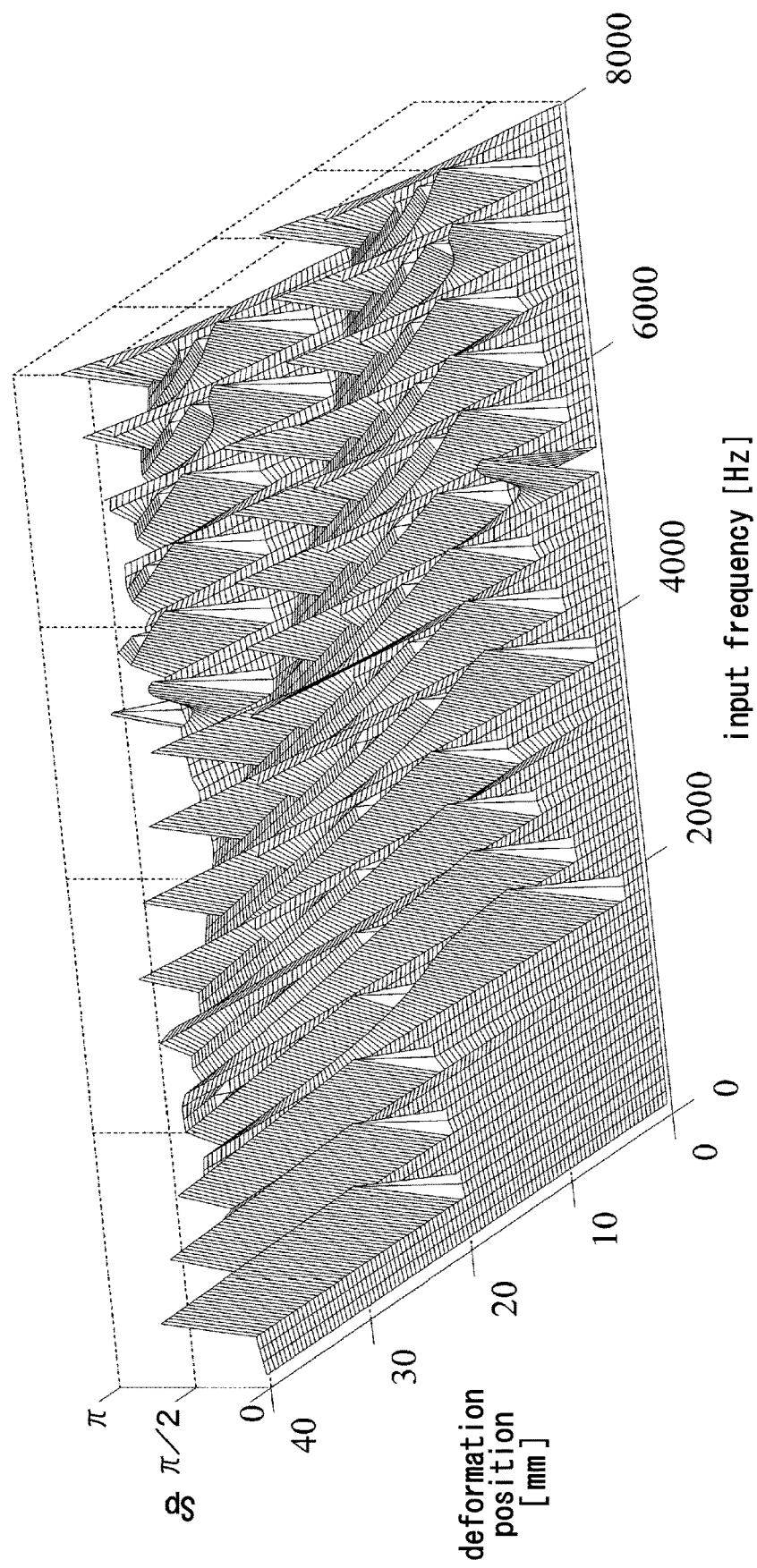
FIG. 33 is a figure that shows the value of a value Sp in accordance with the input frequency $f_{in}$ and the deformation position xp.
Figure 34:
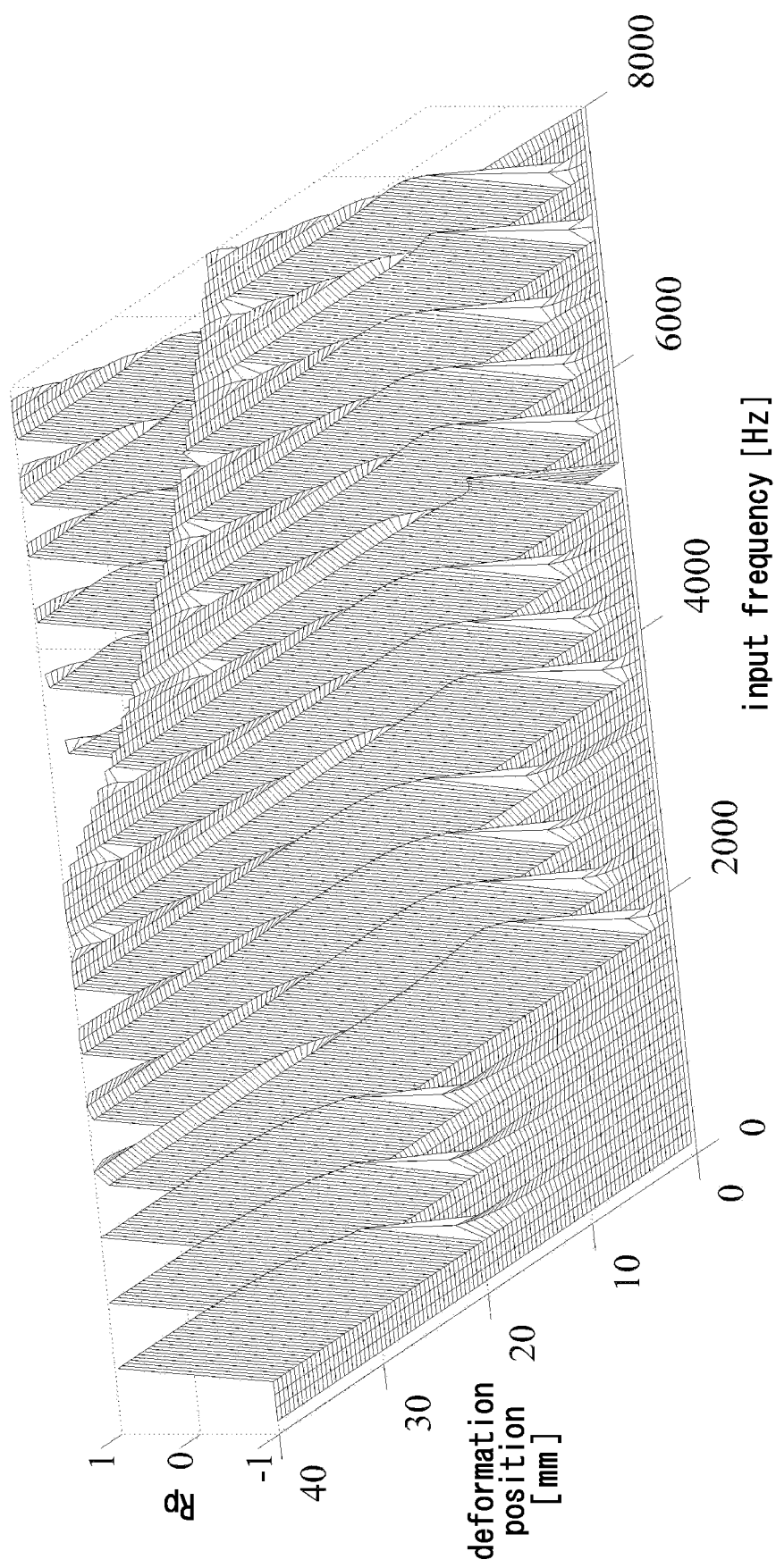
FIG. 34 is a figure that shows the value of a value Rp in accordance with the input frequency $f_{in}$ and the deformation position xp.

Next, the results of the analysis when Ep is used as the sensor output will be explained. FIG. 33 shows the value of Sp that is calculated by Equation (4) in relation to each combination of ($f_{in}$, xp). It can be seen that the overall trend is similar to that in FIG. 31. Focusing on the region where Sp is not less than 3π/4, FIG. 33 indicates the possibility that, because the surface area is small, the output range will vary greatly when the input frequency or the deformation position fluctuate. Focusing on the region where Sp is not less than π/4 and not greater than π/2, it can be seen that the output range is relatively wide in relation to the input frequency and the deformation position. In the region where Sp is close to π/2, it can be seen that the output range decreases by one-half, but no problems arise as long as the phase difference is measured with good sensitivity. Next, FIG. 34 shows the value of Rp that is calculated by Equation (5) in relation to each combination of ($f_{in}$, xp). In the same manner as in FIG. 32, there are few regions where the absolute value of Rp is close to zero (for example, the region where the absolute value of Rp is not greater than 0.1), which are regions where the linearity is poor, and it can be seen that the linearity is good for almost all combinations of ($f_{in}$, xp). Therefore, in a case where the control commands that correspond to the phase difference ϕ are output to the haptic presentation device 6, the tactile stimuli that are provided by the haptic presentation device 6 make it possible for the operator 90 to perceive the displacement of the elastic film 10″ by the lump. However, it has been shown that, depending on how the design parameters are selected, the slope varies as the deformation position changes, so when the phase difference is used, it is necessary to select the design parameters to avoid this variation in the slope.

Based on the results of the analysis as described above, it can be seen that the output range and the linearity exhibit broadly similar trends when the squared intensity ratio F and the phase difference ϕ are used. However, the measurement of the phase difference ϕ is comparatively complicated, because the input sound must also be measured. In contrast, the measurement of the squared intensity ratio F can be conducted independently of the input of the sound, so it is easier to use.

(Sixth Embodiment)

Next a sixth embodiment of the present invention will be explained with reference to FIGS. 35 and 36. In the sixth embodiment, the tip sensor portion 20" in the fifth embodiment is replaced by a tip sensor portion 20'''. Except for the tip sensor portion, the configuration is the same as in the fifth embodiment.

The tip sensor portion 20''' is configured from an elastic tube 10''', which is made of silicone rubber, and a back plate 11''', which is made of acrylic. The elastic tube 10''' is a cylindrical member with no bottom that extends almost straight in the same direction as the longitudinal direction of the rigid tube 12, and it is made of the same material as the elastic film 10" in the fifth embodiment. The outside diameter of the elastic tube 10''' is 6 millimeters, for example, and its width is such that it can be passed through the hole 91c. The inside diameter of the elastic tube 10''' is 4 millimeters, for example. The length of the elastic tube 10''' in the longitudinal direction is 30 millimeters, for example. The total length of the contact detection instrument 1 of the present embodiment is 360 millimeters.

Figure 35:
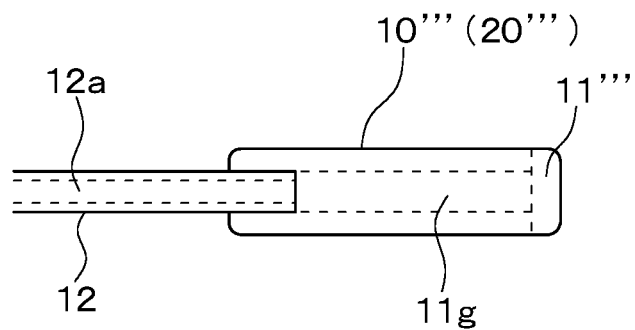
FIG. 35 is an oblique view of a tip sensor portion 20''' according to a sixth embodiment.

As shown in FIG. 35, a hollow space 11g is formed in the interior of the elastic tube 10'''. The hollow space 11g has an opening at the rigid tube 12 end of the elastic tube 10'''. One end of the rigid tube 12 is inserted into the opening, making the hollow space 11g continuous with the hollow space 12a. Furthermore, at the opposite end of the elastic tube 10''' from the rigid tube 12, the hollow space 11g is sealed by the back plate 11'''.

Therefore, the elastic tube 10''' covers and seals off the hollow spaces 13a, 12a, and 11g, and when the elastic tube 10''' is pressed from outside the contact detection instrument 1, the elastic tube 10''' is deformed such that it is pressed inward toward the hollow spaces.

The longitudinal direction of the hollow space 11g is the same as the longitudinal direction of the elastic tube 10''' and is orthogonal to the circumferential direction of the tip sensor portion 20'''. Therefore, in the present embodiment, the direction in which the elastic tube 10''' follows the contour of the internal organ 91b is orthogonal to the longitudinal direction of the hollow space 11g.

The operation of the contact detection instrument 1 of the present embodiment is the same as in the fifth embodiment. Accordingly, when the operator 90 inserts the contact detection instrument 1 of the present embodiment into the internal organ 91b through the hole 91c and follows the contour of the internal organ 91b with the side face of the elastic tube 10''', if the elastic tube 10''' is deformed by coming into contact with a lump inside the living body 91, the signal that the microphone 15 outputs also changes accordingly. Therefore, the presence of a lump inside the living body can be detected.

Figure 36:
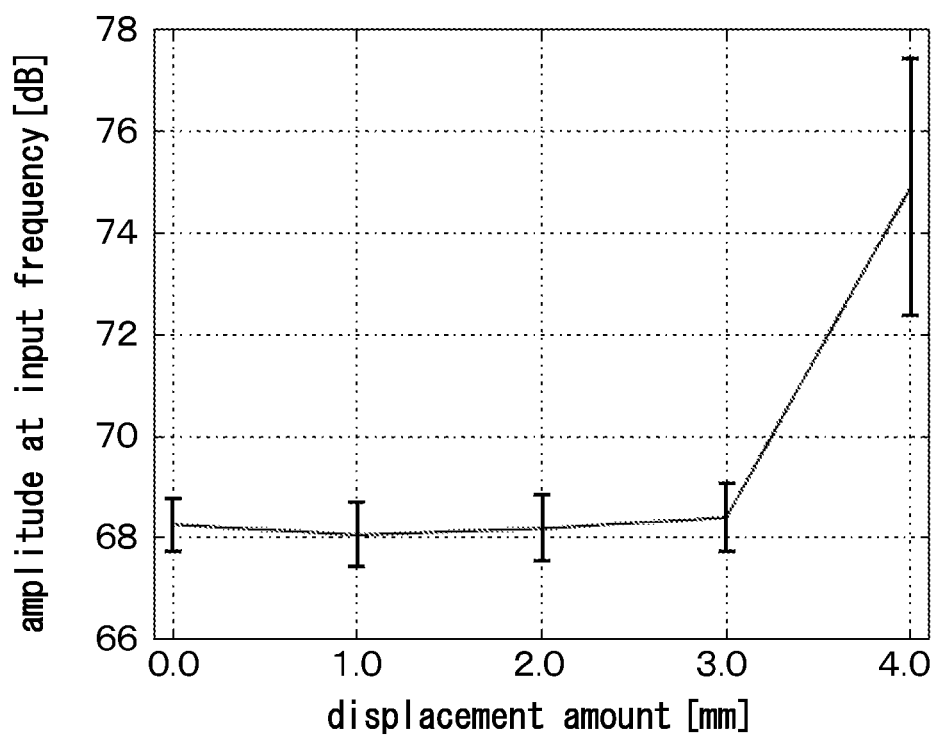
FIG. 36 is a figure that shows experimental results for the sixth embodiment.

FIG. 36 shows the results of an experiment on the amount of displacement of the elastic tube 10''' and the change in the sound pressure level of the composite sound 24 in relation to the input sound 21 in a case where the frequency of the input sound 21 is set at 2670 Hz. The experiment was conducted five times. It can be seen from the figure that the sound pressure level tends to become greater as the displacement becomes greater. Even in the range where the deformation is low, a slight change can be seen in accordance with the deformation amount.

(Other Embodiments)

Note that the present invention is not limited to the embodiments that are described above, and modifications can be made as desired within the scope of the claims. Furthermore, the embodiments that are described above are not wholly unrelated, and they can be combined as desired, except in cases where a combination is clearly not possible. Moreover, in the embodiments that are described above, it goes without saying that the elements that make up the embodiments are not absolutely necessary, except in cases where it is clearly stated that they are particularly necessary, cases where they are thought to be clearly necessary in principle, and the like. Further, in each of the embodiments that are described above, the structural elements of the embodiment are not limited to a specific number, except in cases where a specific numerical value is stated for the number of elements, numerical values, quantities, ranges, and the like, case where it is clearly stated that a specific number is particularly necessary, cases where a specific number is thought to be clearly necessary in principle, and the like. Furthermore, in each of the embodiments that are described above, when a shape, a positional relationship, or the like is stated for a structural element or the like, the structural element or the like is not limited to that shape, positional relationship, or the like, except in cases where a limit is specifically stated, cases where the structural element or the like is clearly limited to a specific shape, positional relationship, or the like in principle, and the like. Further, for the present invention, modified examples such as those hereinafter described are permitted for each of the embodiments that are described above. Note that the modified examples hereinafter described can be selected independently to be applied or not applied to the embodiments that are described above. That is, any desired combination of modified examples hereinafter described can be applied to the embodiments that are described above.

(Modified Example 1)

The scope of application of the sensing system of the present invention is not limited to laparoscopic surgery, and the system can also be applied to other endoscopic surgeries, such as thoracoscopoic surgery and the like, provided that they are surgical procedures in which the contact detection instrument 1 is inserted into a living body through a hole that has been opened in the surface of the living body.

The sensing system of the present invention can also be applied to non-endoscopic surgeries, provided that they are surgical procedures in which the contact detection instrument 1 is inserted into a living body through a hole that has been opened in the surface of the living body. In those cases, the endoscope 7, the cable 8, and the image display device 9 are not required.

(Modified Example 2)

In each of the embodiments that are described above, the haptic presentation device 6 provides the tactile stimuli to the sole of the foot of the operator 90, but that does not necessarily have to be the case. For example, the haptic presentation device 6 may be wrapped around the leg (for example, the ankle) of the operator 90 and provide the tactile stimuli to the leg. To take another example, the haptic presentation device 6 may be attached not only to the lower body of the operator 90, but also to the upper body, such as the midsection, the chest, and the like, such that the tactile stimuli are provided to the upper body.

(Modified Example 3)

In each of the embodiments that are described above, the contact detection instrument 1 is used as a simple sensing instrument and is not furnished with a scissors function for cutting the internal organ 91b of the living body 91. However, that does not necessarily have to be the case, and the contact detection instrument 1 may also be furnished with a scissors function for cutting the internal organ 91b of the living body 91.

(Modified Example 4)

In the embodiments that are described above, the tip base portions 11, 11" are made of ABS resin, but they may also be made of hard rubber. The tip base portions 11, 11" need only to have a greater Young's modulus (that is, be harder) than the elastic films 10, 10".

(Modified Example 5)

In the embodiments that are described above, the haptic presentation device 6 provides the tactile stimuli to the operator 90 based on the signal that is output from the microphone 15, but the signal from the microphone 15 may also be transmitted to the operator 90 in a different form. For example, based on the signal that is output from the microphone 15, an image presentation device may present to the operator 90 an image that corresponds to the signal (for example, a graph of the squared intensity ratio F, or a graph of the phase difference $\phi$).

(Modified Example 6)

In the embodiments that are described above, the number of the stimulators that the haptic presentation devices 6, 93, 94 have is either one or three, but the number of the stimulators may also be two, four, or more. Furthermore, the number of degrees of freedom of the tactile stimuli that the haptic presentation device provides may be one, two, three, or more.

(Modified Example 7)

In each of the embodiments that are described above, a single tone, that is, a sound that has only one frequency component, is used as the input sound 21, but that does not necessarily have to be the case, that is, a sound that has a plurality of discrete frequency components may also be used as the input sound 21. The amplitude and the phase differences would thus be detected for each frequency in the input sound and the composite sound, and using that information would make it possible to measure the deformation amount and the deformation position with greater precision.

(Modified Example 8)

In the first to the fourth embodiments that are described above, the combination of H1, H2, H3 and the combination of θ1, θ2 that the control commands specify are basically determined based on the view that the force that bears on the elastic film 10 (that is, the amount of pressing, the deformation amount, or the reflection rate r) is independent of the phase difference $\phi$ and dependent on the squared intensity ratio F, and that the deformation position xp is independent of the squared intensity ratio F and dependent on the phase difference $\phi$.

However, the correspondence relationship between the combination of H1, H2, H3 (or the combination of θ1, θ2) and the combination of the squared intensity ratio F and the phase difference $\phi$ may be determined more accurately by experimentation or the like, and the correspondence relationship that is thus determined may be converted to data in the form of a correspondence relationship table or the like and stored in the control unit 4. In that case, based on the data, the control unit 4 would determine the combination of H1, H2, H3 (or the combination of θ1, θ2) from the computed values for the squared intensity ratio F and the phase difference $\phi$.

(Modified Example 9)

The elastic films 10, 10" in the embodiments that are described above cover and seal off only the openings in the side faces of the tip base portions 11, 11" (the openings that connect the hollow spaces 11d, 11f) and the area around them. However, this does not necessarily have to be the case. For example, edges (seams in the elastic films) are not formed in the tip sensor portions 20, 20", so the elastic films 10, 10" may also cover the entire tip base portions 11, 11". In that case, the portions of the elastic films 10, 10" that cover the hollow spaces 11d, 11f may be made slightly thicker, such that the sensing portion (the portion that covers the hollow spaces 11d, 11f) is clearly indicated, the elastic films 10, 10" will make contact more firmly with the tissue of the living body, and the elastic films 10, 10" will be pressed more deeply into the hollow spaces 11d, 11f.

REFERENCE SIGNS LIST 1, 1' Contact detection instrument
6, 93, 94 Haptic presentation device
10, 10" Elastic film (Elastic material)
10', 10''' Elastic pipe (Elastic material)
11, 11', 11", 11' Tip base portion
12 Rigid tube (Rod)
13 Grip portion
14 Speaker
15 Microphone
20, 20', 20", 20''' Tip sensor portion

The invention claimed is:

1. A contact detection instrument configured to be inserted into an interior of a living body, the contact detection instrument comprising:
   a rod;
   a sensor portion attached to the rod and configured to be inserted into the interior of the living body;
   a speaker configured to input, from outside the living body, a sound into a hollow space formed in an interior of the rod and in an interior of the sensor portion, the sensor portion including an elastic material covering at least one portion of the hollow space; and
   a microphone configured to remain outside the living body and to output an electrical signal corresponding to the sound inside the hollow space inputted by the speaker.

2. The contact detection instrument according to claim 1, wherein the at least one portion of the hollow space covered by the elastic material is oriented in a first direction in which the sound inputted into the hollow space by the speaker is transmitted, the at least one portion of the hollow space extending along a circumferential direction of the sensor portion in a vicinity of the elastic material.

3. The contact detection instrument according to claim 1, wherein the at least one portion of the hollow space covered by the elastic material is oriented in a first direction in which the sound inputted into the hollow space by the speaker is transmitted, the at least one portion of the hollow space extending in a winding direction around a central axis of the sensor portion in a vicinity of the elastic material.

4. The contact detection instrument according to claim 1, wherein:
   the rod extends straight, and
   the at least one portion of the hollow space covered by the elastic material is oriented in a first direction in which the sound inputted into the hollow space by the speaker is transmitted, the at least one portion of the hollow space extending along a circumferential direction of the rod in a vicinity of the elastic material.

5. The contact detection instrument according to claim 1, wherein:
   the rod extends straight, and
   the at least one portion of the hollow space covered by the elastic material is oriented in a first direction in which the sound inputted into the hollow space by the speaker is transmitted, the at least one portion of the hollow space extending in a winding direction around a central axis of the rod in a vicinity of the elastic material.

6. A sensing system comprising:
the contact detection instrument according to claim 1;
a haptic presentation device configured to provide a tactile stimulus to a user based on the electrical signal outputted from the microphone; and
a control unit configured to control the haptic presentation device based on the electrical signal outputted from the microphone of the contact detection instrument.

7. The sensing system according to claim 6, wherein the haptic presentation device is configured to provide the tactile stimulus to a lower body of the user.

8. The sensing system according to claim 6, wherein the haptic presentation device is configured to provide the tactile stimulus to a sole of a foot of the user.

9. The sensing system according to claim 6, wherein the haptic presentation device is configured to (i) provide the tactile stimulus to the user with at least two degrees of freedom, and (ii) provide the tactile stimulus to the user in at least two locations.

10. The contact detection instrument according to claim 1, wherein the at least one portion of the hollow space covered by the elastic material extends in an arc shape along a direction in which the sound inputted into the hollow space by the speaker is transmitted.

11. The contact detection instrument according to claim 10, wherein a longitudinal direction of the sensor portion, in the at least one portion of the hollow space covered by the elastic material, is orthogonal to the direction in which the sound inputted into the hollow space by the speaker is transmitted.

12. The contact detection instrument according to claim 10, wherein the arc shape of the at least one portion of the hollow space covered by the elastic material has a radius of curvature no greater than 3.5 millimeters.

13. The contact detection instrument according to claim 10, wherein:
the sensor portion includes a base portion attached to the elastic material, and
the arc shape of the at least one portion of the hollow space covered by the elastic material has a radius of curvature no greater than one-half of an outside diameter of the base portion.

14. The contact detection instrument according to claim 1, wherein the at least one portion of the hollow space covered by the elastic material extends in an arc shape along a longitudinal direction of the hollow space.

* * * * *